United States Patent [19]

Martin et al.

[11] Patent Number: 5,428,053
[45] Date of Patent: Jun. 27, 1995

[54] 1-AMINOACETAMIDOPYRROLES AND 1-AMINO ACETAMIDO-2-(SUBSTITUTED) PYRROLES AND RELATED COMPOUNDS

[75] Inventors: Lawrence L. Martin, Lebanon; Raymond W. Kosley, Jr.; Denise M. Flanagan, both of Bridgewater, all of N.J.; Gert U. Kuerzel, Hofheim, Germany; Peter A. Nemoto, Raritan; David G. Wettlaufer, Phillipsburg, both of N.J.

[73] Assignee: Hoechst-Roussel Pharmaceuticals Inc., Somerville, N.J.

[21] Appl. No.: 102,181

[22] Filed: Sep. 28, 1993

Related U.S. Application Data

[62] Division of Ser. No. 922,291, Jul. 30, 1992, Pat. No. 5,274,116.

[51] Int. Cl.$^6$ .............. A61K 31/40; C07D 207/50; C07D 403/06
[52] U.S. Cl. .................. 514/422; 514/343; 514/423; 514/426; 546/281; 548/518; 548/527; 548/539; 548/540; 548/557
[58] Field of Search ............. 548/518, 527, 539, 540, 548/557; 546/281; 514/343, 422, 423, 426

[56] References Cited

U.S. PATENT DOCUMENTS

| | | | |
|---|---|---|---|
| 4,517,195 | 5/1985 | Effland et al. | 514/413 |
| 4,588,727 | 5/1986 | Effland et al. | 514/255 |

FOREIGN PATENT DOCUMENTS

| | | |
|---|---|---|
| 0167922 | 1/1986 | European Pat. Off. |
| 0308912 | 3/1989 | European Pat. Off. |
| 1184770 | 3/1970 | United Kingdom ............ 548/557 |

OTHER PUBLICATIONS

Jones, D. W., "Reaction of Phthalimidonitrene with Furans", *J.C.S. Perkin I*, No. 21, 1972, pp. 2728-2731.

Jacobi, P. A. et al., "A Novel Synthesis of Pyrromethenones", *Tetrahedron Letters*, vol. 29 No. 38, 1988 pp. 4823-4826.

Hamer, R. et al., "Synthesis of 5-Phenylpyrrolo[1,2,6][1,2,5]-triazepin-2(3H)-ones[1]", *J. Heterocyclic Chemistry*, vol. 25, No. 2, 1988, pp. 517-521.

*Primary Examiner*—Mary C. Lee
*Assistant Examiner*—Jacqueline Haley
*Attorney, Agent, or Firm*—Elliott Korsen

[57] ABSTRACT

There are disclosed 1-aminoacetamidopyrroles and 1-amino-2-(substituted) pyrroles and related compounds of the formula

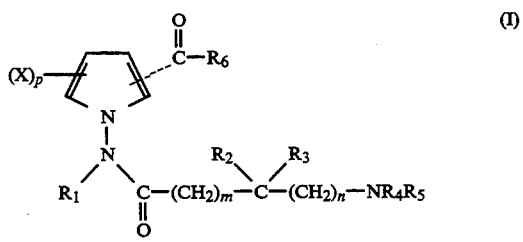
(I)

wherein all substituents are defined herein, which are useful as glycine partial agonists and for the enhancement of learning and memory and for the treatment of memory dysfunctions associated with neurodegenerative disorders and are thus indicated in the treatment of Alzheimer's disease and other senile dementias.

43 Claims, No Drawings

1-AMINOACETAMIDOPYRROLES AND 1-AMINO ACETAMIDO-2-(SUBSTITUTED) PYRROLES AND RELATED COMPOUNDS

This is a division of application Ser. No. 07/922,291 filed Jul. 30, 1992 now U.S. Pat. No. 5,274,116.

The present invention relates to compounds of the general formula

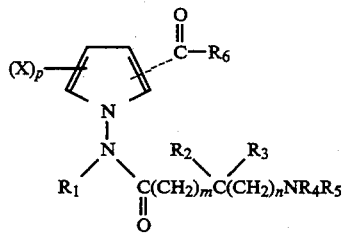

(I)

wherein
- $R_1$ is hydrogen or loweralkyl;
- $R_2$ is hydrogen, loweralkyl, hydroxyloweralkyl, acyloxyloweralkyl or loweralkoxyloweralkyl;
- $R_3$ is hydrogen or loweralkyl;
- or $R_2$ and $R_3$ taken together form a $C_3$–$C_7$ cycloalkyl ring;
- $R_4$ is hydrogen, loweralkyl, aryl or arylloweralkyl;
- $R_5$ is hydrogen, loweralkyl, acyl, aryloxycarbonyl, loweralkoxycarbonyl or arylloweralkoxycarbonyl;
- X is hydrogen, halogen, cyano, loweralkyl, aryl, arylloweralkyl, hydroxyloweralkyl, arylhydroxyloweralkyl, aminoloweralkyl, loweralkylaminoloweralkyl, diloweralkylaminoloweralkyl, arylsulfonyl or loweralkylsulfonyl;
- m and n are independently 0–5, with the proviso that the sum of m and n does not exceed 5;
- p is 0, 1 or 2;

and when the dotted line between the pyrrole ring and the carbonyl group represents a bond, $R_6$ is hydrogen, hydroxy, loweralkyl, loweralkoxy, amino, loweralkylamino, diloweralkylamino,

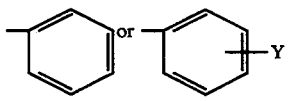

where Y is hydrogen, halogen, loweralkyl, loweralkoxy, hydroxy, trifluoromethyl or nitro, or heteroaryl selected from

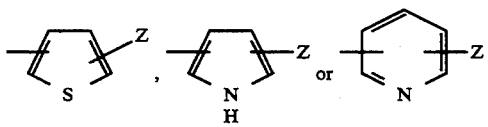

where Z is hydrogen, halogen or loweralkyl, with the proviso that when m and n are each zero and when $R_2$ and $R_3$ are each hydrogen and $R_6$ is phenyl or substituted phenyl and together with the carbonyl group is attached at the 2-position of the pyrrole ring, Y cannot be hydrogen, halogen, trifluoromethyl or nitro;

or a pharmaceutically acceptable addition salt thereof or, where applicable, an optical or geometrical isomer or racemic mixture thereof.

The compounds of this invention are useful as glycine partial agonists and for the enhancement of learning and memory and in the treatment of memory dysfunction associated with neurodegenerative disorders and are thus indicated in the treatment of Alzheimer's disease and other senile dementias.

Additionally, this invention relates to novel compounds of the formula

(II)

and

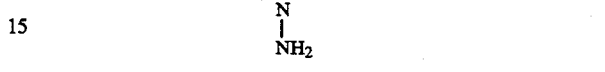

(III)

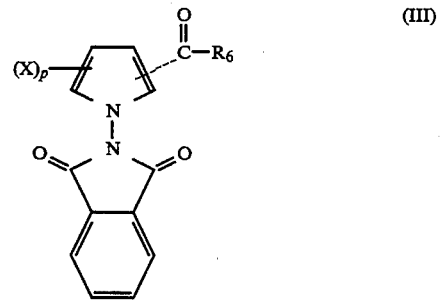

where X, p and $R_6$ are as previously defined, which are useful as intermediates in the preparation of the target compounds of this invention.

This invention also relates to a novel method of use for 2-benzoylpyrrole glycinamides which were disclosed in U.S. Pat. Nos. 4,517,195 and 4,588,727. These compounds were previously disclosed as being useful as analgesic, anxiolytic or anticonvulsant agents. It has been found that the 2-benzoylpyrroles are also useful as glycine partial agonists and for the enhancement of learning and memory and in the treatment of memory dysfunction associated with neurodegenerative disorders.

Unless otherwise stated or indicated, the following definitions shall apply throughout the specification and appended claims.

The term lower shall mean the group it is describing contains from 1 to 6 carbon atoms.

The term loweralkyl shall mean a straight or branched alkyl group having from 1 to 6 carbon atoms, e.g., methyl, ethyl, n-propyl, isopropyl, n-butyl, isobutyl, sec-butyl, t-butyl and straight and branched chain pentyl and hexyl.

The term halogen shall mean fluorine, chlorine, bromine or iodine.

The term aryl shall mean a phenyl group substituted with 0, 1 or 2 substituents each of which is independently loweralkyl, loweralkoxy, halogen, trifluoromethyl or nitro or a fluorenyl group.

The term acyl shall mean a group of the formula

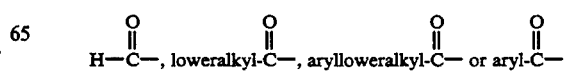

where loweralkyl and aryl are as defined above.

Throughout the specification and appended claims, a given chemical formula or name shall encompass all stereo and optical isomers where such isomers exist.

In one preferred embodiment of this invention are compounds (IV) of the formula

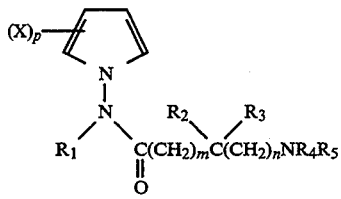
(IV)

where $R_1$ to $R_5$, X, m, n and p are as previously defined.

In another preferred embodiment of this invention are compounds (V) of the formula

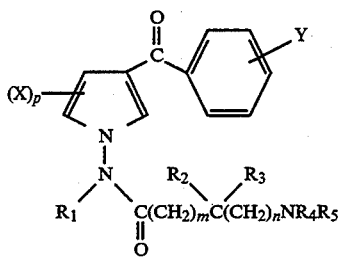
(V)

where $R_1$ to $R_5$, X, Y, m, n and p are as defined above.

In a third preferred embodiment of this invention are compounds of the formula

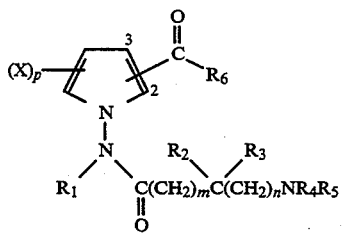
(VI)

wherein the group

is attached to the pyrrole at either the 2- or 3-position and $R_6$ is loweralkyl or a heteroaryl group selected from

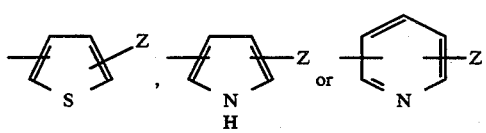

where Z is as previously defined.

The compounds of this invention are prepared in the following manner. The substituents $R_1$, $R_2$, $R_3$, $R_4$, $R_5$, $R_6$, X, m, n and p are as defined above unless indicated otherwise.

PREPARATION OF THE INVENTION

To prepare compounds (IV) of the formula

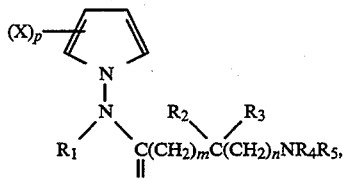
(IV)

1-phthalimidopyrrole of the formula

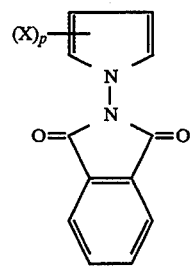

is treated with a suitable base such as methylamine or hydrazine to remove the phthalimido group to give a 1-aminopyrrole of the formula

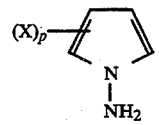

This reaction is generally carried out in a polar organic solvent such as dimethylformamide at a temperature of about 0° to 150° C., preferably 20° to 25° C., for 0.5 to 18 hours.

1-Phthalimidopyrrole can be prepared using the method disclosed in Flitsch et al., Chem. Ber. 1969, 102, pp. 3268–3276.

A 1-aminopyrrole is reacted with compound (VII) of the formula

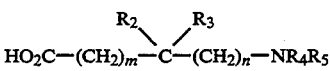
(VII)

where $R_5$ is a protecting group such as, but not limited to, loweralkoxycarbonyl or arylloweralkoxycarbonyl, in the presence of a condensing agent such as, but not limited to, dicyclohexylcarbodiimide (DCC) or diisopropylcarbodiimide to yield a compound of formula (VIII)

(VIII)

This reaction is typically conducted in a suitable solvent such as dichloromethane, dimethylformamide or tetrahydrofuran at a temperature of 0° to 100° C., preferably 20° to 25° C., for 0.5 to 18 hours. Typically the reaction is carried out at ambient temperature under stirring for about 4 hours. The reaction may be conducted in the presence of an inert gas such as nitrogen or argon.

The protecting group of the compound of formula (VIII) can be removed by means known in the art. For instance, where $R_5$ is carbobenzyloxy (CBZ), it can be removed by hydrogenolysis of compound (VIII) in the presence of a noble metal catalyst such as palladium on carbon or palladium on barium sulfate to yield compound (IX).

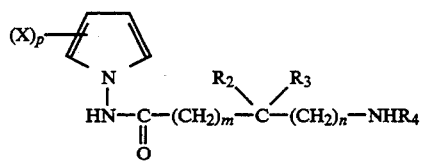

Typically, this reaction is carried out in a suitable solvent such as methanol, ethanol or isopropanol at a temperature of 20° to 60° C.

Where $R_5$ is a t-butyoxycarbonyl moiety, the group may be hydrolyzed in the presence of a strong acid such as hydrochloric, hydrobromic or trifluoroacetic acid in an organic solvent such as ethyl acetate, tetrahydrofuran, chloroform, methanol or ethanol at a temperature of 0° to 60° C., preferably 0° to 25° C., to yield compounds of formula (IX).

To prepare compounds where $R_1$ of formula (I) is loweralkyl, compound (VIII) is reacted with an appropriate alkylating agent such as a loweralkylhalide, e.g. iodomethane or bromopropane or a diloweralkyl sulfate, e.g. dimethylsulfate or diethylsulfate, in the presence of a suitable base to yield compound (X) of the formula

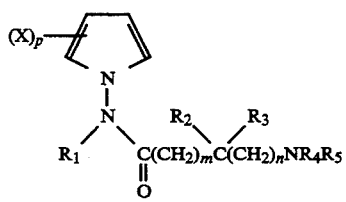

where $R_1$ is loweralkyl.

To prepare compounds where $R_2$ is acyloxyloweralkyl, compound (VIII) where $R_2$ is loweralkanol is reacted with an anhydride, $(R_7CO_2)_2O$, or mixed anhydride in the case of formic-acetic anhydride, where $R_7$ is hydrogen or loweralkyl in the presence of pyridine. This reaction is typically carried out at a temperature of 0° to 60° C. for 0.5 to 18 hours.

To prepare compounds (XI) of the formula

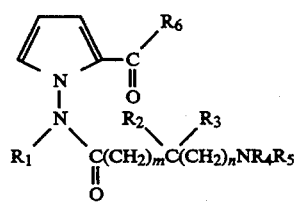

where $R_6$ is loweralkyl, 1-phthalimidopyrrole is reacted with acetyl chloride or other suitable acylating agents to afford compound (XII) of the formula

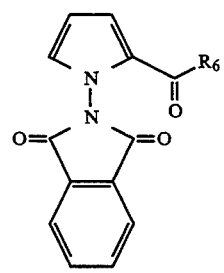

Compound (XII) is subsequently treated with a suitable base, preferably methylamine, in a polar organic solvent such as dimethylformamide to yield compound (XIII) of the formula

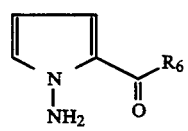

Compound (XIII) is reacted with a compound of the formula

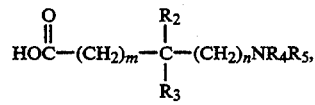

where $R_5$ is a protecting group such as t-butoxycarbonyl or carbobenzyloxy, to yield compound (XI), where $R_5$ is a protecting group such as t-butoxycarbonyl or carbobenzyloxy, which is subsequently deprotected as earlier described to yield compound VI of the formula

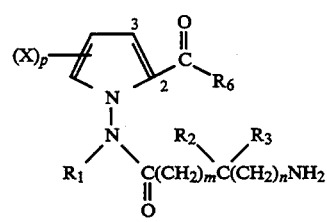

To prepare compound (XI) where $R_6$ is heteroaryl, 1-phthalimidopyrrole is reacted with an appropriate agent such as a heteroaryl-substituted carboxylic acid or heteroaryl carbonyl chloride. When the carboxylic acid is employed, the acid is reacted in a suspension of a suitable solvent such as dichloromethane with oxalyl chloride or other suitable agent. A catalyst such as tin (IV) chloride is added and the 1-phthalimidopyrrole is introduced portionwise over a period of 15 to 60 minutes. This reaction typically takes place at a temperature of about −40° to 0° C. for 0.5 to 2 hours. When the heteroaryl substituted carbonyl chloride is employed, similar steps are taken, however, oxalyl chloride is not used.

The resultant heterocarbonyl substituted phthalimide is treated with a suitable base such as methylamine to remove the phthalimido group and yield the corresponding 1-aminopyrrole compound. This reaction is generally carried out in a polar organic solvent such as dimethylformamide at a temperature of about 0° to 40° for 0.5 to 24 hours. Said heteroarylcarbonyl substituted 1-aminopyrrole is subsequently reacted as described earlier to yield the aminoacetamidoheteroarylacylpyrroles.

The 3-benzoylaminopyrroles and derivatives of the formula

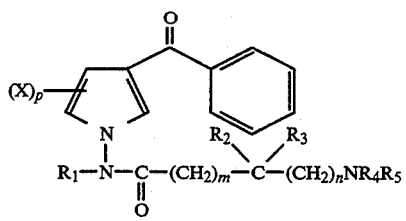

are prepared in the following manner.

A 3-benzoylpyrrole of the formula

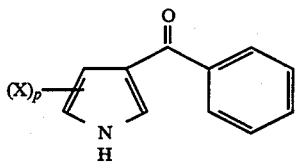

in potassium hydroxide or other suitable base is reacted with hydroxylamine-O-sulfonic acid to yield a 1-amino-3-benzoylpyrrole of the formula

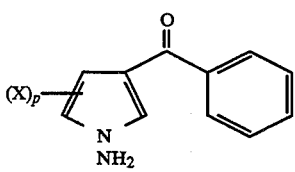

This reaction typically takes place in the presence of a suitable solvent such as dimethylformamide at a temperature of about 0° to 25° C. (or at room temperature) for 0.5 to 4 hours.

Compound (XVII) is subsequently reacted with a compound of formula (VII) where $R_5$ is loweralkoxycarbonyl or aryloweralkoxycarbonyl to yield compound (XV).

Compound (XV) is subsequently deprotected treated as previously described to yield compound (XVIII).

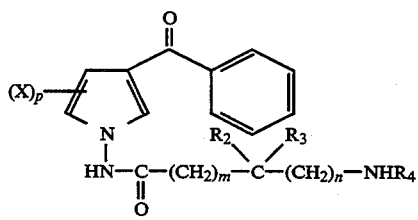

To prepare compounds of formula (I) where X is halogen, 1-phthalimidopyrrole is reacted with a halogenating agent such as N-chlorosuccinimide or N-bromosuccinimide, optionally in the presence of a catalyst such as azobis(isobutyronitrite) to obtain the desired compounds. Typically, this reaction is carried out in a suitable organic solvent such as dimethylformamide or carbon tetrachloride at a temperature of about 20° to 45° C. for 1 to 3 hours.

To prepare compounds of formula (I) wherein m or $n \geq 2$, that is, with further extension of the glycinamide chain, an amino acid such as 4-aminobutyric acid or β-alanine is reacted with a base such as triethylamine or pyridine and an amino-protecting reagent such as 2-(t-butoxycarbonyloxyimino)-2-phenylacetonitrile. The N-protected amino acid formed is subsequently reacted as previously described with 1-aminopyrrole and N,N'-dicyclohexylcarbodiimide to give the desired products.

The compounds of the present invention are useful as glycine partial agonists and for the enhancement of learning and memory and in the treatment of memory dysfunction associated with neurodegenerative disorders and are thus indicated in the treatment of Alzheimer's disease and other senile dementias.

These utilities are manifested in the following in vitro and in vivo assays.

[$^3$H]GLYCINE BINDING

Purpose

This assay is used to assess the affinity of compounds for the glycine binding site associated with the N-methyl-D-aspartate (NMDA) receptor complex using [$^3$H]glycine as the radioligand.

Introduction

The amino acid glycine modulates and may be a requirement for the activation of the excitatory amino acid receptors of the NMDA-subtype. Glycine has been shown in vitro to potentiate the effects of 1-glutamate or NMDA on the stimulation of [$^3$H]TCP binding (TCP=1-[1-(2-thienyl)cyclohexyl]piperidine) and [$^3$H]norepinephrine release and in vivo to act as a positive modulator of the glutamate-activated cGMP response in the cerebellum. The activation of NMDA receptors requiring the presence of glycine is necessary for the induction of long-term potentiation (LTP), a type of synaptic plasticity which may be fundamental to learning process. A [$^3$H]glycine binding site in the brain has been identified and characterized as a strychnine-insensitive site associated with the NMDA receptor complex. Autoradiographic studies have shown a similar distribution of [$^3$H]glycine and [$^3$H]TCP (NMDA ion channel radioligand) binding sites. Compounds which interact with this glycine site offer a novel mechanism of action for modulation of NMDA receptor function.

Procedure

This procedure is a modification of the method described by Monahan et al.[1]

A. Reagents

1. Buffer A: 0.5M Tris maleate, pH 7.4 59.3 g Tris maleate bring to 0.5 l Adjust pH to 7.4 with 0.5M Tris base
2. Buffer B: 50 mM Tris maleate, pH 7.4 Dilute Buffer A 1:10 with distilled water, adjust pH with 50 mM Tris maleate (acid) or 50 mM Tris base.
3. Glycine, $5 \times 10^{-2}$M Dissolve 3.755 mg of glycine with 1.0 ml distilled water. Aliquots of 20 μl to the assay tube will give a final concentration of $10^{-3}$M.
4. [$^3$H]Glycine is obtained from New England Nuclear, specific activity 45–50 Ci/mmole. For IC$_{50}$ determinations, a 200 nM stock solution is made with distilled water. Aliquots of 50 μl are added to yield a final assay concentration of 10 nM.

5. Test compounds. A stock solution of 5 mM is made with a suitable solvent and serially diluted, such that the final concentration in the assay ranges from $10^{-4}$ to $10^{-7}$M. Higher or lower concentrations may be used, depending on the potency of the compound.

6. Triton-X 100, 10% (v/v). A stock solution of Triton-X 100, 10% can be prepared and stored in the refrigerator. Dilute 1.0 ml of Triton-X 100 to 10.0 ml with distilled water. On the day of the assay, the tissue homogenate (1:15 dilution) is preincubated with an aliquot of the 10% solution to give a final concentration of 0.04% (v/v).

B. Tissue Preparation

Cortices of male Wistar rats are dissected over ice and homogenized in ice-cold 0.32M sucrose (1:15 w/v) for 30 seconds with a Tissumizer setting at 70. Three cortices are pooled for one preparation. The homogenate is centrifuged at 1,000 g for 10 minutes. The supernatant is centrifuged at 20,000 g for 20 minutes. Resuspend the pellet in 15 volumes of ice-cold distilled water (Tissumizer setting 70, 15 sec) and spin at 7,600 g for 20 minutes. Save the supernatant, swirl off the upper buffy layer of the pellet and add to the supernatant. Centrifuge the supernatant at 48,000 g for 20 minutes. Resuspend the pellet with 15 volumes of cold distilled water and centrifuge. Discard the supernatant and store the pellet at −70° C.

On the day of the assay, resuspend the pellet in 15 volumes ice-cold 50 mM Tris maleate, pH 7.4. Preincubate the homogenate with Triton-X in a final concentration of 0.04% (v/v) for 30 minutes at 37° C. with agitation. Centrifuge the suspension at 48,000 g for 20 minutes. Wash the pellet an additional 3 times by resuspension with cold buffer and centrifugation. The final pellet is resuspended in a volume 25 times the original net weight.

C. Assay

1. Prepare assay tubes in triplicate.

| | |
|---|---|
| 380 μl | Distilled water |
| 50 μl | Buffer A, 0.5M Tris maleate, pH 7.4 |
| 20 μl | Glycine, $10^{-3}$M final concentration, or distilled water or appropriate concentration of inhibitor |
| 50 μl | [³H] Glycine, final concentration 10 nM |
| 500 μl | Tissue homogenate |
| 1000 μl | Final volume |

2. Following the addition of the tissue, the tubes are incubated for 20 minutes in an ice-bath at 0°–4° C. Terminate the binding by centrifugation for 20 minutes. Return the tubes to ice. Aspirate and discard the supernatant. Carefully rinse the pellet twice with 1 ml ice-cold buffer, avoiding disruption of the pellet. Transfer the pellet to scintillation vials by vortexing the pellet with 2 ml of scintillation fluid, rinse the tubes twice with 2 ml and add an additional 4 ml of scintillation fluid.

3. Specific binding is determined from the difference of binding in the absence or presence of $10^{-3}$M glycine and is typically 60–70% of total binding. IC$_{50}$ values for the competing compound are calculated by log-probit analysis of the data.

Reference:
1. Monahan, J. B. et al., J. Neurochem. 53, 370–375 (1989).

ENHANCEMENT OF [³H]TCP BINDING

Glutamate is considered to be a major excitatory neurotransmitter in the central nervous system. In addition, glutamate has been postulated as being involved in a number of pathological conditions such as neuronal damage and loss due to ischemic stress (e.g. stroke), and in neurodegenerative disorders including Huntington's disease, amyotrophic lateral sclerosis, neurolathyrism, Alzheimer's disease and others. A central dopaminergic-glutamatergic balance was also suggested as important for both akinetic motor disorders (e.g. Parkinson's disease) and psychosis (e.g. schizophrenia).

Postsynaptic effects of glutamate are mediated by a variety of glutamate receptor subtypes, which are classified as N-methyl-D-aspartate (NMDA) and non-NMDA (quisqualate, kainate) receptor subtypes. Of the glutamate receptor subtypes, the NMDA receptor has been extensively investigated. The receptor is composed of an agonist binding site (the NMDA site), and a cation channel with binding sites for magnesium and other ligands including PCP, TCP and dextromethorphan. A number of modulatory sites associated with the NMDA receptor have been identified, including binding sites for zinc, polyamines and glycine. The glycine site may provide a therapeutic target for treatment of various types of cognitive impairments including Alzheimer's disease.

The glycine modulatory site (glycine B site) is insensitive to strychnine whereas a strychnine sensitive glycine binding site associated with spinal cord neurons has been designated as the glycine A site. In extensively washed preparations of rat cortical membranes, NMDA increases the specific binding of [³H]TCP in a concentration dependent manner (EC$_{50}$=3.1 μM) and addition of glycine (1 μM) potentiates the maximal effect of NMDA by a factor of 1.7. This preparation may be used to evaluate the effect of compounds at the NMDA associated strychnine-insensitive glycine modulatory site. Compounds can be characterized as agonists (compounds producing an effect equivalent to the maximal effect of glycine) or partial agonists (compounds producing less than the maximal effect of glycine) at this site. The prototypical glycine partial agonist is D-cycloserine.

Procedure

This procedure is a modification of the method described by Snell et al.[1]

Crude synaptosomal homogenates were prepared from cortical tissue obtained from male Sprague Dawley rats immediately after sacrifice or that had been frozen at 60° C. for not more than one month. Tissue was homogenized by Polytron in ice-cold 0.32M sucrose and centrifuged for 20 minutes at 1000 g. The resulting supernatant was decanted and recentrifuged at 17,500 g. The resulting pellet was then resuspended in 50 vols. of ice cold distilled water and lysed at 37° C. for 30 minutes followed by centrifugation at 36,000 g for 20 minutes. The resulting pellet was carried through a second lysing and then washed by resuspension in 50 vols. of 10 mM HEPES: Na HEPES buffer (pH 7.5). The homogenate was centrifuged again (36,000 g; 20 minutes), resuspended in 30 vols. of HEPES buffer and frozen at −60° C. until used for binding experiments. On the day of the assay, the homogenate was thawed and washed three times with 30 vols. of buffer before use. There were no appreciable difference in the binding in homogenates obtained from fresh compared to frozen tissue.

All binding studies were performed by incubating homogenates (approximately 0.2 mg protein per assay tube) with 2.5 nM [$^3$H]TCP (obtained from New England Nuclear, 40 Ci/mmol) for 120 minutes at 25° C. in a final volume of 1 ml. Non-specific binding was determined in the presence of 100 μM PCP. The assay tubes were prepared in triplicate as follows:

| | |
|---|---|
| 360 μl | distilled water |
| 50 μl | 0.1M HEPES buffer, pH 7.5 |
| 20 μl | L-glutamic acid, 5 × 10$^{-6}$M (final concentration = 10$^{-7}$M) |
| 20 μl | glycine, final concentration 10$^{-8}$ to 10$^{-3}$M, or compound final concentration 10$^{-8}$ to 10$^{-3}$M, or distilled water, or PCP, final concentration 100 μM |
| 50 μl | [$^3$H]TCP |
| 500 μl | Tissue homogenate |
| 1000 μl | Final volume |

The binding reaction was terminated by vacuum filtration on GF/C glass fiber filters which were presoaked for 20–30 minutes in 0.05% polyethyleneimine in order to reduce binding to the filters. Filtration was followed by 2 washes with 4 ml of ice-cold buffer and the retained radioactivity was measured by liquid scintillation spectrometry. Protein concentration was measured by the method of Bradford, Anal. Biochem., 72 (1976), 248–354.

Reference:
1. L .D. Snell et al., Neuroscience Letters, 83, 313–317 (1987).

Results of some of the compounds of the invention in the above assays are presented below in Table 1.

TABLE 1

| [$^3$H]GLYCINE BINDING | | ENHANCEMENT OF [$^3$H]TCP BINDING | |
|---|---|---|---|
| COMPOUND | IC$_{50}$ (μM) | EC$_{50}$ (μM) | % OF MAXIMAL GLYCINE RESPONSE (CONCENTRATION μM) |
| 2-amino-N-[2-(2-fluoro-benzoyl)-1H-pyrrol-1-yl]-actamide hydrobromide hemihydrate | 11.2 | 3.1 | 77(10) |
| 2-amino-N-1H-pyrrol-1-ylacetamide hydrochloride | 14.8 | 92 | 65(100) |
| N-(2-acetyl-1H-pyrrol-1-yl)-2-aminoacetamide hydrochloride | 22.5 | 1.3 | 71(10) |
| 2-amino-N-[2-(2-thienyl-carbonyl)-1H-pyrrol-1-yl]acetamide hydrochloride | 6.0 | 0.38 | 78(10) |
| 2-amino-N-[2-(2-chloro-benzoyl)-1H-pyrrol-1-yl]-acetamide hydrochloride | 22.5 | 3.0 | 56(10) |
| 2-amino-N-[2-(4-methoxy-benzoyl)-1H-pyrrol-1-yl]-acetamide hydrochloride | 6.6 | 2.0 | 89(100) |
| 2-amino-N-[5-chloro-2-(2-fluorobenzoyl)-1H-pyrrol-1-yl]acetamide hydrobromide | 6.0 | 1.7 | 65(30) |
| 2-amino-N-[2-(3-fluoro-benzoyl)-1H-pyrrol-1-yl]-acetamide fumarate | 4.8 | 0.6 | 76(10) |
| glycine (ref.) | 0.13 | 0.056 | 100 |
| D-cycloserine (ref.) | 2.5 | 1.8 | 80 |

ENHANCEMENT OF STEP-DOWN PASSIVE AVOIDANCE IN RATS

Compounds which enhance either glycine or acetylcholine transmission have been shown to significantly increase a rat's passive avoidance latency to "step-down" compared to vehicle treated animals. In this assay, rats step off a wooden platform and subsequently receive a low-level foot shock. After 24 hours, the rats are observed for their ability to acquire and remember a passive avoidance behavior, that is, to stay on the platform.

Male Sprague Dawley rats (Charles River) weighing 275–325 g were used in the passive avoidance procedure. Following a 1½ week acclimation to the vivarium (5 rats per cage) where food and water were available ad libitum, rats were transported to the laboratory on day 1 of testing and acclimated to the experimental area and the investigator. Rats were labeled (tails marked) and handled by the investigator, then gently placed on a wooden platform (14×10.5×3.5 cm) in the experimental chamber (30.5×25×27 cm.) The chamber is equipped with a single house light and white noise generator to mask extraneous sounds. Once the animal stepped off the platform (all 4 paws touching the grid floor where grids are equally spaced every 2 cm), it was picked up by the base of the tail and returned to the home cage and then to the vivarium.

On day 2, rats were returned to the laboratory and again acclimated to the experimental area for 30 min. Rats were intraperitoneally administered vehicle or compounds 30 min. prior to testing in a dosage volume of 1 ml/kg. Then the rats were gently placed on the wooden platform and their latency (in sec.) to step-down was recorded. When all four paws touched the grid, a low level 0.28 mA electric shock was delivered for 3 sec. by means of a Coulbourn Instruments grid floor shocker. Rats were immediately removed from the experimental chamber to their home cage when the shock ceased. Rats which did not step down within 60 sec. were pushed off the platform in order to receive the electric shock. Fifteen minutes later, this procedure was repeated. Rats were then returned to the vivarium.

On day 3, rats were returned to the laboratory and following a 30 min. acclimation to the experimental area, gently placed on the wooden platform and their latency to step-down (no shock) was measured.

The latencies of each drug group on day 3 (24 hrs. following acquisition) was compared to the latencies of the vehicle control group by the non-parametric Mann-Whitney U test. Groups which showed a significant increase in their median latency to step-down compared to controls were considered to show an enhancement of learning.

Results of some of the compounds of the invention in this assay are presented in Table 2.

TABLE 2

| Compound | Dose (mg/kg,ip) | % Change from Control |
|---|---|---|
| 2-amino-N-[2-(2-fluoro-benzoyl)-1H-pyrrol-1yl]-acetamide hydrobromide hemihydrate | 10 | +471 |
| | 20 | +836 |
| 2-amino-N-1H-pyrrol-1-ylacetamide hydrochloride | 10 | +281 |
| | 20 | +625 |
| | 80 | +512 |
| 2-amino-N-[2-(2-trifluoro-methyl)benzoyl)-1H-pyrrol 1-yl]acetamide hydrobromide | 5 | +900 |
| | 10 | +77 |
| | 20 | +122 |
| | 40 | +33 |
| 2-amino-N-[2-(2-methoxy-benzoyl)-1H-pyrrol-1-yl]-acetamide hydrochloride | 1.25 | +237 |
| | 2.5 | +114 |
| | 5 | +80 |
| | 10 | +37 |
| 2-amino-N-(2-chloro-1H-pyrrol-1-yl)acetamide hydrochloride | 10 | +158 |
| | 20 | +25 |
| | 40 | +133 |
| 2-amino-N-[2-(3-fluorobenzoyl)-1H-pyrrol-1-yl]acetamide fumarate | 2.5 | +286 |
| | 5 | +457 |
| | 10 | +343 |
| | 20 | +257 |
| D-cycloserine (ref) | 2.5 | +253 |
| | 5.0 | +120 |

T-MAZE REINFORCED ALTERNATION TASK IN RATS

Male Wistar rats (Charles River) weighing 450-700 g were used in the T-maze procedure. Rats were housed (3 rats per cage) under standard laboratory conditions in the vivarium where food and water were available ad libitum. During training and testing, animals were transported to the dimly lit test room and acclimated for 30 min. The Lafayette Instruments T-maze consisted of a start box (30×20 cm), an alley way to the choice point (30×20 cm), a choice point area (25×25 cm), and two goal areas (30×20 cm) with a shock grid (grids every 1½ cm) serving as the floor of the maze. Each session in the maze was controlled by a microprocessor.

Initially, animals were trained to greater than 70% choice accuracy in the maze for five consecutive days each week over a two week period. Following a 10 min. habituation to the maze, training commenced. All reinforced alternation sessions consisted of ten pseudo randomly paired trials. The first trial of each pair was the forced trial where the animal was forced to go to either the left or right goal box, since only one goal box door was open. The second trial was the choice trial where both goal box doors were open and the correct response was to enter the opposite goal to that entered on the previous forced run trial.

Each trial began when the rat was placed in the start box and allowed 15 sec. to enter the appropriate goal box. If the rat did not leave the start box or enter a goal box within 15 sec., a 0.4 mA intermittent electric shock (1 sec. on, 2 sec. off) was delivered by a Lafayette Instruments shock scrambler until the rat reached the appropriate goal box resulting in the simultaneous termination of shock and closing of the goal box guillotine door. Following a 30 sec. intertrial interval (ITI), the next trial commenced. If during the choice trial, the rat entered the incorrect goal box (same goal entered during the forced trial), the guillotine door was closed and the rat received 5 electric shocks during the first 15 sec. of the 30 sec. ITI. All choices and latencies during the 10 paired trials were recorded by the computer controlled printer.

Animals which met criteria during training ($\geq$ correct choices) were considered trained colony animals and were tested every other week. Testing was conducted over 3 consecutive days. Control sessions for baseline responding were conducted on days 1 and 2 so that the mean percentage of correct choices for each animal to qualify for drug testing was set at $\geq$70% correct choices.

First, rats were administered scopolamine at 1 mg/kg, i.p. (30 min. pretreatment) which resulted in overall responding at chance levels (=50% choice accuracy). The next time these animals were tested, they were administered pharmacological agents i.p. (at appropriate pretreatment times) in combination with scopolamine to measure effectiveness in reversing scopolamine-induced deficits in choice accuracy.

For statistical analysis, the means of each treatment group (drug+scopolamine) were compared to the mean of both the scopolamine alone group and the control group by the Dunnett's test.

Results of some of the compounds of the invention in this assay are presented in Table 3.

TABLE 3

| Treatment (i.p.) | Dose (mg/kg) | Mean % of Correct Choice |
|---|---|---|
| Vehicle | | 82 |
| Scopolamine | 1 | 45 |
| Scopolamine w/D-cycloserine | 1/3 | 59 |
| Scopolamine w/D-cycloserine | 1/10 | 61 |
| Scopolamine w/2-amino-N-[2-(2-fluorobenzoyl)-1H-pyrrol-1-yl]acetamide hydrobromide hemihydrate | 1/20 | 64 |

The enhancement of memory and learning and treatment of memory dysfunction associated with neurodegenerative disorders is achieved when the compounds of this invention are administered to a subject requiring such treatment at an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administeration of the aforesaid compound. It is to be further understood that the dosages set forth herein are exemplary only and they do not to any extent, limit the scope of the invention.

Effective quantities of the compounds of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ™, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:

(±)-1,1-dimethylethyl-[1-methyl-2-oxo-2-(1H-pyrrol-1-ylamino)ethyl]carbamate;

(±)-phenylmethyl-[1-methyl-2-oxo-2-(1H-pyrrol-1-ylamino)ethyl]carbamate;

(±)-2-amino-N-1H-pyrrol-1-ylpropanamide;

1,1-dimethylethyl-[2-oxo-2-(1H-pyrrol-1-ylamino)ethyl]carbamate;

phenylmethyl-[2-oxo-2-(1H-pyrrol-1-ylamino)ethyl]carbamate;

2-amino-N-1H-pyrrol-1-ylacetamide;

(S)-phenylmethyl-[1-methyl-2-oxo-2-(1H-pyrrol-1-ylamino)ethyl]carbamate;

(S)-2-amino-N-1H-pyrrol-1-ylpropanamide;

1,1-dimethylethyl-[1-[(1H-pyrrol-1-ylamino)carbonyl]-cyclopropyl]carbamate;

1-amino-N-1H-pyrrol-1-ylcyclopropanecarboxamide;

1,1-dimethylethyl-[1-[(1H-pyrrol-1-ylamino)carbonyl]-cyclopentyl]carbamate;

1-amino-N-1H-pyrrol-1-ylcyclopentanecarboxamide;

(S)-phenylmethyl-[1-(hydroxymethyl)-2-oxo-2-(1H-pyrrol-1-ylamino)ethyl]carbamate;

(S)-2-amino-3-hydroxy-N-1H-pyrrol-1-ylpropanamide;

(R)-phenylmethyl-[1-methyl-2-oxo-2-(1H-pyrrol-1-ylamino)ethyl]carbamate;

(R)-2-amino-N-1H-pyrrol-1-ylpropanamide;

(±)-phenylmethyl-[1-(hydroxymethyl)-2-oxo-2-(1H-pyrrol-1-ylamino)ethyl]carbamate;

(±)-2-amino-3-hydroxy-N-1H-pyrrol-1-ylpropanamide;

(±)-phenylmethyl-[1-(acetyloxymethyl)-2-oxo-2-(1H-pyrrol-1-ylamino)ethyl]carbamate;

(±)-3-(acetyloxy)-2-amino-N-1H-pyrrol-1-ylpropanamide;

2-[2-(4-methoxybenzoyl)-1H-pyrrol-1-yl]-1H-isoindole-1,3(2H)dione;

(1-amino-1H-pyrrol-2-yl)(4-methoxyphenyl)methanone;

phenylmethyl-[2-[[2-(4-methoxybenzoyl)-1H-pyrrol-1-yl]amino]-2-oxoethyl]carbamate;

2-amino-N-[2-(4-methoxybenzoyl)-1H-pyrrol-1-yl]acetamide;

(1-amino-1H-pyrrol-3-yl)phenylmethanone;

phenylmethyl-[2-[(3-benzoyl-1H-pyrrol-1-yl)amino]-2-oxoethyl]carbamate;

2-[2-(2-thienylcarbonyl)-1H-pyrrol-1-yl]-1H-isoindole-1,3-(2H)dione;

(1-amino-1H-pyrrol-2-yl)-2-thienylmethanone;

1,1-dimethylethyl-[2-oxo-2[[2-(2-thienylcarbonyl)-1H-pyrrol-1-yl]amino]ethyl]carbamate;

2-amino-N-[2-(2-thienylcarbonyl)-1H-pyrrol-1-yl]acetamide;

2-[2-(1H-pyrrol-2-ylcarbonyl)-1H-pyrrol-1-yl]-1H-isoindole-1,3(2H)dione;

(1H-amino-1H-pyrrol-2-yl]-1H-pyrrol-2-ylmethanone;

phenylmethyl-[2-oxo-2-[[2-(1H-pyrrol-2-ylcarbonyl)-1H-pyrrol-1-yl]-amino]ethyl]carbamate;

2-amino-N-[2-(1H-pyrrol-2-ylcarbonyl)-1H-pyrrol-1-yl]acetamide;

2-(2-acetyl-1H-pyrrol-1-yl)-1H-isoindole-1,3(2H)dione;

1-(1-amino-1H-pyrrol-2-yl)ethanone;

phenylmethyl-[2-[(2-acetyl-1H-pyrrol-1-yl)amino]-2-oxoethyl]carbamate;

1,1-dimethylethyl-[2-[(2-acetyl-1H-pyrrol-1-yl)amino]-2-oxoethyl]carbamate;

N-(2-acetyl-1H-pyrrol-1-yl)-2-aminoacetamide;

1,1-dimethylethyl-[4-oxo-4-(1H-pyrrol-1-ylamino)-butyl]carbamate; and 1,1-dimethylethyl-[3-oxo-3-(1H-pyrrol-1-ylamino)-propyl]carbamate.

The following examples are for illustrative purposes and are not to be construed as limiting the invention disclosed herein. All temperatures are given in degrees centigrade (°C.) unless indicated otherwise.

EXAMPLE 1

(±)-1,1-Dimethylethyl-[1-methyl-2-oxo-2-(1H-pyrrol-1-ylamino)ethyl]carbamate

To a stirred solution consisting of racemic N-(tert-butoxycarbonyl)alanine, (6.69 g) and N-aminopyrrole (3.19 g) in dichloromethane (hereinafter DCM) (354 ml) was added N-N'-dicyclohexylcarbodiimide (hereinafter DCC) (7.66 g) at 0° C. under nitrogen. After stirring for 24 hours at room temperature, the reaction mixture was filtered through a pad of celite and the solid dicyclohexylurea (hereinafter DCU) was washed with DCM. Concentration of the filtrate gave the crude product as a solid. Purification via flash column chromatography (silica gel, 5–25% ethyl acetate/hexane) afforded 3.52 g of the product as a solid, m.p. 170°–174° C.

Analysis: Calculated for $C_{12}H_{19}N_3O_3$: 56.90%C 7.56%H 16.59%N Found: 57.18%C 7.06%H 16.46%N

EXAMPLE 2

(±)-Phenylmethyl-[1-methyl-2-oxo-2-(1H-pyrrol-1-ylamino)ethyl]carbamate

To a stirred solution consisting of carbobenzyloxy-D,L-alanine (10.0 g) and N-aminopyrrole (3.68 g) in dry DCM (224 ml) was added DCC (9.71 g) at room temperature under nitrogen. After stirring for 20 hours, the reaction mixture was filtered through a pad of celite and the solid DCU was washed with DCM. Concentration of the filtrate gave the crude product. Purification via flash column chromatography (silica gel, 30% ethyl acetate/hexane) afforded 8.50 g of the product as a solid, m.p. 153°–155° C.

Analysis: Calculated for $C_{15}H_{17}N_3O_3$: 62.71%C 5.96%H 14.62%N Found: 62.49%C 5.86%H 14.47%N

EXAMPLE 3

(±)-2-Amino-N-1H-pyrrol-1-ylpropanamide Hydrochloride

The carbobenzyloxy group (hereinafter CBZ) of racemic phenylmethyl-[1-methyl-2-oxo-2-(1H-pyrrol-1-ylamino)ethyl]carbamate (3.27 g) was cleaved in a minimal volume of methanol over 5% Pd-C (0.65 g) with $H_2(g)$ (278 ml) under atmospheric conditions. The catalyst was removed by filtration through a pad of celite and the filter cake was washed with methanol. The combined filtrates were concentrated and the product purified via flash column chromatography (silica gel, 70% methanol/hexane) affording 1.50 g of the product as an oil. The hydrochloride salt was prepared in ether/methanol (10:1) with ethereal HCl, m.p. 213°–215° C.

Analysis: Calculated for $C_7H_{12}ClN_3O$: 44.33%C 6.38%H 22.16%N Found: 44.20%C 6.39%H 21.69%N

EXAMPLE 4

1,1-Dimethylethyl-[2-oxo-2-(1H-pyrrol-1-ylamino)ethyl]carbamate

To a solution of 1-aminopyrrole (1.64 g) in dry DCM (50 ml) were added N-tert-butoxycarbonylglycine (3.50 g) and DCC (4.12 g) under cooling of the flask in an ice-water bath. After a few minutes the cooling bath was removed and the reaction mixture was stirred for 4 hours at ambient temperature. The precipitate was removed by filtration and the filtrate evaporated to dryness. The residue was purified by flash column chromatography (silica gel, ethyl acetate/n-hexane 50:50). Recrystallization from diethyl ether/n-hexane afforded 3.82 g of the product as crystals, m.p. 85°–86° C.

Analysis: Calculated for $C_{11}H_{17}N_3O_3$: 55.22%C 7.16%H 17.56%N Found: 55.42%C 6.82%H 17.52%N

EXAMPLE 5

Phenylmethyl-[2-oxo-2-(1H-pyrrol-1-ylamino)ethyl]carbamate

To a solution of 1-aminopyrrole (2.46 g) and carbobenzyloxyglycine (6.28 g) in 120 ml of dry DCM and 10 ml of dry dimethylformamide was added DDC (8.00 g). The reaction mixture was stirred at room temperature over a period of 64 hours. The precipitate was removed by filtration and stirred in boiling ethyl acetate. The mixture was filtered and the filtrate was combined with the filtrate of the reaction mixture and evaporated to dryness. The residue was purified by flash column chromatography (silica gel, DCM/methanol 20:1) yielding a first fraction (2.97 g) which was contaminated by DCU. A second fraction recrystallized from ethyl acetate afforded 1.54 g of the product as crystals, m.p. 146°–147° C.

Analysis: Calculated for $C_{14}H_{15}N_3O_3$: 61.53%C 5.53%H 15.38%N Found: 61.45%C 5.44%H 15.24%N

EXAMPLE 6a

2-Amino-N-1H-pyrrol-1-ylacetamide Hydrochloride

To 1,1-dimethylethyl-[2-oxo-2-(1H-pyrrol-1-ylamino)ethyl]carbamate (5.67 g) was added 35 ml of a 3.7M ethereal hydrogen chloride solution. The reaction mixture was stirred at room temperature over a period of 5 hours. The colored powder obtained by suction filtration was purified by addition of a solution of the product in methanol/diethyl ether, collecting the precipitate and repeating this procedure several times until the greater part of the substance was dissolved in the mother liquors. The last precipitate was discarded and the combined mother liquors were again recrystallized from methanol/diethyl ether. This afforded 1.90 g (46%) of the product as a powder, m.p. 212°–215° C. (dec.).

Analysis: Calculated for $C_6H_{10}ClN_3O$: 41.04%C 5.74%H 23.93%N Found: 40.84%C 5.65%H 23.60%N

EXAMPLE 6b

2-Amino-N-1H-pyrrol-1-ylacetamide Hydrochloride

The CBZ group of phenylmethyl-[2-oxo-2-(1H-pyrrol-1-ylamino)ethyl]carbamate (8.8 g) was cleaved in a minimal volume of methanol over 5% Pd-C (1.3 g) with $H_2(g)$ (787 ml) under atmospheric conditions. The catalyst was removed via filtration through a pad of celite and the filter cake was washed with methanol. The combined filtrates were concentrated and the remaining residue was purified via flash column chromatography (silica gel, EtOAc/0–30% methanol) affording 4.1 g of the desired product as an oil. The hydrochloride salt was prepared in methanol/ether with ethereal HCl, m.p. 215° C. (dec.).

Analysis: Calculated for $C_6H_{10}ClN_3O$: 41.04%C 5.74%H 23.93%N Found: 41.02%C 5.80%H 23.87%N

EXAMPLE 7

(S)-Phenylmethyl-[1-methyl-2-oxo-2-(1H-pyrrol-1-ylamino)ethyl]carbamate

To a stirred solution of carbobenzyloxy-L-alanine (10.0 g) and N-aminopyrrole (3.68 g) in dry DCM (224 ml) was added DCC (9.71 g) at 0° C. under nitrogen. The cooling bath was removed after ten minutes and the reaction mixture was allowed to stir at room temperature for 17 hours. The mixture was filtered and the solid DCU filter cake was washed with hot ethyl acetate. Concentration of the combined filtrate gave the crude product. Recrystallization from ethyl acetate/hexane afforded 10.46 g of the product as a solid, m.p. 169°–171° C.

Analysis: Calculated for $C_{15}H_{17}N_3O_3$: 62.71%C 5.96%H 14.62%N Found: 62.67%C 6.08%H 14.44%N

EXAMPLE 8

(S)-2-Amino-N-1H-pyrrol-1-ylpropanamide

The CBZ group of (S)-phenylmethyl-[1-methyl-2-oxo-2-(1H-pyrrol-1-ylamino)ethyl]carbamate (5.50 g) was cleaved in a minimal volume of methanol over 5% Pd-C (0.83 g) with $H_2(g)$ (468 ml) under atmospheric conditions. The catalyst was removed by filtration through a pad of celite and the filter cake was washed with methanol. The combined filtrate was concentrated and the residue purified via flash column chromatography (silica gel, 20% EtOH/ethyl acetate) to afford 2.62 g of the desired product as an oil which crystallized on standing, m.p. 81°–82° C.

Analysis: Calculated for $C_7H_{11}N_3O$: 54.89%C 7.24%H 27.43%N Found: 55.15%C 7.20%H 27.23%N

EXAMPLE 9

1,1-Dimethylethyl-[1-[(1H-pyrrol-1-ylamino)carbonyl]cyclopropyl]carbamate

To a stirred solution 1-amino-1-cyclopropanecarboxylic acid hemihydrate (1.70 g) in acetone/water (50 ml, 1:1) was added triethylamine (3.20 ml) and 2-(tert-butoxycarbonyloxyimino)-2-phenylacetonitrile (4.18 g) at room temperature. After stirring for 24 hours, the reaction mixture was concentrated in vacuo and diluted with water and ethyl acetate. The layers were separated and the aqueous phase was washed twice with ethyl acetate and then acidified with 5% citric acid (aq.). The N-protected amino acid was then extracted with ethyl acetate 6times. The combined organic extracts were washed with brine, dried (MgSO4), filtered and concentrated to give 2.90 g of 1-[N-(tert-butoxycarbonyl)]-1-cyclopropanecarboxylic acid as a solid, which was used without further purification.

To a stirred solution of the protected amino acid (2.84 g) and 1-aminopyrrole (1.27 g) in dry DCM (100 ml) and dry tetrahydrofuran (41 ml) was added DCC (3.06 g) at 0° C. under nitrogen. After stirring for 72 hours at room temperature, the precipitated DCU was removed via filtration. Concentration of the filtrate gave the crude product as a solid. Purification via flash column chromatography (silica gel, 30% ethyl acetate/hexane) afforded 1.95 g of the product as a solid, m.p. 160°–162° C.

Analysis: Calculated for $C_{13}H_{19}N_3O_3$: 58.85%C 7.22%H 15.84%N Found: 59.23%C 7.30%H 15.59%N

EXAMPLE 10

1-Amino-N-1H-pyrrol-1-ylcyclopropanecarboxamide Hydrochloride

To a stirred solution consisting of 1,1-dimethylethyl-[1-[(1H-pyrrol-1-ylamino)carbonyl]cyclopropyl]carbamate (3.18 g) in ethyl acetate/isopropanol (70 ml) was added excess ethereal HCl. After stirring for 48 hours at room temperature, the reaction appeared complete by thin layer chromatography (TLC) (silica gel, 30% EtOAc/hexane, $I_2$ stain). The solid product was filtered under nitrogen and recrystallized from ether/ethanol to afford 1.20 g of the product as a solid, m.p. 238°–240° C.

Analysis: Calculated for $C_8H_{12}ClN_3O$: 47.65%C 6.00%H 20.84%N Found: 47.57%C 6.00%H 20.60%N

EXAMPLE 11

1,1-Dimethylethyl-[1-[(1H-pyrrol-1-ylamino)carbonyl]cyclopentyl]carbamate

To a stirred solution consisting of 1-(1-tert-butoxycarbonylamino)cyclopentanecarboxylic acid, (6.39 g) and N-aminopyrrole (2.29 g) in dry DCM (140 ml) was added DCC (6.04 g) at room temperature under nitrogen. After stirring for 72 hours at room temperature, the reaction mixture was filtered through a pad of celite and the filter cake was washed with DCM. Concentration of the filtrate gave the crude product as a solid. Purification via flash column chromatography (silica gel, 30% EtOAc/hexane) afforded 4.12 g of the product as a solid, m.p. 188°–189° C.

Analysis: Calculated for $C_{15}H_{23}N_3O_3$: 61.41%C 7.90%H 14.32%N Found: 61.79%C 7.92%H 14.18%N

EXAMPLE 12

1-Amino-N-1H-pyrrol-1-ylcyclopentanecarboxamide Hydrochloride

To a stirred solution consisting of 1,1-dimethylethyl-[1-[(1H-pyrrol-1-ylamino)carbonyl]cyclopentyl]carbamate (2.90 g) in ethyl acetate/isopropanol (30 ml, 3:1) was added excess ethereal HCl. After stirring for 18 hours at room temperature, the reaction appeared complete by TLC (silica gel, 30% EtOAc/hexane, $I_2$ stain). The solid was filtered under nitrogen and recrystallized from ether/methanol to afford 1.40 g of the product, m.p. 218°–220° C.

Analysis: Calculated for $C_{10}H_{16}ClN_3O$: 52.29%C 7.02%H 18.29%N Found:

EXAMPLE 13

(S)-Phenylmethyl-[1-(hydroxymethyl)-2-oxo-2-(1H-pyrrol-1-ylamino)ethyl]carbamate To a solution of 1-aminopyrrole (3.28 g) and carbobenzyloxy-L-serine (9.57 g) in 100 ml of dry DCM and 10 ml of dry dimethylformamide was added DCC (10.0 g) at 0° C. After 10 minutes the ice bath was removed and the reaction mixture was stirred at room temperature overnight. The precipitate was filtered and stirred in boiling ethyl acetate. The mixture was filtered and the filtrate was combined with the filtrate of the reaction mixture and evaporated to dryness. The residue was purified by flash column chromatography (silica gel, DCM/methanol 20:1). The appropriate fractions were concentrated and the residue recrystallized from ethyl acetate to afford 7.48 g of the product as crystals, m.p. 163°–164° C.

Analysis: Calculated for $C_{15}H_{17}N_3O_4$: 59.40%C 5.65%H 13.85%N Found: 59.52%C 5.64%H 13.81%N

EXAMPLE 14

(S)-2-Amino-3-hydroxy-N-1H-pyrrol-1-ylpropanamide (S)-Phenylmethyl-[1-(hydroxymethyl)-2-oxo-2-(1H-pyrrol-1-ylamino)ethyl]carbamate (4.90 g) was dissolved in 100 ml of methanol over 5% Pd/C (500 mg). The solution was hydrogenated at atmospheric pressure and room temperature until absorption of 80% of the theoretical amount of hydrogen. The catalyst was removed by filtration and the filtrate was evaporated to dryness. The residue was purified by flash column chromatography (silica gel, ethyl acetate/methanol 4:1) to afford the desired product as a powder. Recrystallization from ethyl acetate/methanol/hexane gave the product as needles (1.37 g), m.p. 135°–137° C.

Analysis: Calculated for $C_7H_{11}N_3O_2$: 49.70%C 6.55% H 24.84%N Found: 49.79%C 6.47%H 24.57%N

EXAMPLE 15

(R)-Phenylmethyl-[1-methyl-2-oxo-2-(1H-pyrrol-1-ylamino)ethyl]carbamate

To a stirred solution consisting of carbobenzyloxy-D-alanine (10.0 g) and N-aminopyrrole (3.68 g) in dry DCM (224 ml) was added DCC (9.71 g) at 0° C. under nitrogen. The cooling bath was removed after ten minutes and the reaction mixture was allowed to stir at room temperature for 24 hours. The suspension was filtered and the DCU filter cake was washed with hot ethyl acetate. Concentration of the filtrate gave the crude product. Recrystallization from EtOAc/hexane afforded 11.69 g of the desired product as a solid, m.p. 172°–174° C.

Analysis: Calculated for $C_{15}H_{17}N_3O_3$: 62.71%C 5.96%H 14.62%N Found: 62.85%C 6.08%H 14.56%N

EXAMPLE 16

(R)-2-Amino-N-1H-pyrrol-1-ylpropanamide

The CBZ group of (R)-phenylmethyl-[1-methyl-2-oxo-2-(1H-pyrrol-1-ylamino)ethyl]carbamate (5.13 g) was cleaved in a minimal volume of methanol over 5% Pd-C (1.03 g) with $H_2(g)$ (436 ml) under atmospheric conditions. The catalyst was removed by filtration through a pad of celite and the filter cake was washed with methanol. The combined filtrates were concentrated and the residue purified via flash column chromatography (silica gel, 30% EtOH/EtOAc), affording 2.11 g of the product as a oil which crystallized on standing, m.p. 63°–66° C.

Analysis: Calculated for $C_7H_{11}N_3O$: 54.89%C 7.24%H 27.43%N Found: 54.63%C 7.11%H 27.03%N

EXAMPLE 17

(±)-Phenylmethyl-[1-(hydroxymethyl)-2-oxo-2-(1H-pyrrol-1-ylamino)ethyl]carbamate To a solution of 1-aminopyrrole (4.92 g) and DCC (6.18 g) in dry DCM (100 ml) was added carbobenzyloxy-D,L-serine (7.18 g) in small portions over a period of about 1 hour. After stirring overnight at room temperature, the precipitate was removed by filtration, and stirred in boiling ethyl acetate. The mixture was filtered and the filtrate was combined with the filtrate of the reaction mixture and evaporated to dryness. The residue was purified by flash column chromatography (silica gel, DCM/methanol 20:1) and the appropriate fractions were concentrated. Recrystallization of the residue from ethyl acetate afforded 4.68 g of the product as a powder, m.p. 153°–154° C.

Analysis: Calculated for $C_{15}H_{17}N_3O_4$: 59.40%C 5.65%H 13.85%N Found: 59.69%C 5.72%H 13.83%N

EXAMPLE 18

(±)-2-Amino-3-hydroxy-N-1H-pyrrol-1-yl-propanamide Hydrochloride (±)-Phenylmethyl-[1-(hydroxymethyl)-2-(oxo-2-(1H-pyrrol-1-ylamino)ethyl]carbamate (5.14 g) was dissolved in 100 ml of methanol and 5% Pd/C (600 mg) was added. The solution was hydrogenated at atmospheric pressure and room temperature until 90% of the theoretical amount of hydrogen has been absorbed. The catalyst was removed by filtration and the filtrate was evaporated to dryness. The residue was purified by flash column chromatography (silica gel, ethyl acetate/methanol, 2:1), affording the free base as a powder (2.40 g). This powder was dissolved in 100 ml of diethyl ether and 10 ml of methanol, and then treated with 10 ml of a 1.7M ethereal hydrogen chloride solution. After stirring for 30 min. the precipitate was collected by filtration and washed with diethyl ether, affording the product as a powder (2.17 g), m.p. 161°–163° C.

Analysis: Calculated for $C_7H_{12}ClN_3O_2$: 40.88% C. 5.88% H 20.43%N Found: 40.83%C 5.83%H 20.23%N

EXAMPLE 19

(±)-Phenylmethyl-[1-(acetyloxymethyl)-2-oxo-2-(1H-pyrrol-1-ylamino)ethyl]carbamate To a stirred solution of (±)-phenylmethyl-[1-(hydroxymethyl)-2-oxo-2-(1H-pyrrol-1-ylamino)ethyl]carbamate (4.26 g) in 100 ml of dichloromethane and 20 ml of dimethylformamide were added acetic anhydride (3.0 ml) and pyridine (2.5 ml). The reaction mixture was stirred overnight at room temperature and then combined with the product from a 5.41 mmol scale reaction which was performed under the same conditions. The reaction mixture was washed with 5% citric acid and water, and dried over magnesium sulfate. After evaporation, the crude product was purified by flash column chromatography (silica gel, DCM/methanol, 30:1). Recrystallization from ethyl acetate/n-hexane afforded the product as a powder (2.96 g, 44%), m.p. 154°–155° C.

Analysis: Calculated for $C_{17}H_{19}N_3O_5$: 59.12%C 5.55%H 12.17%N Found: 58.86%C 5.07%H 12.05% N

EXAMPLE 20

(±)-3-(Acetyloxy)-2-amino-N-1H-pyrrol-1-ylpropanamide (±)-Phenylmethyl-[1-(acetyloxymethyl)-2-oxo-2-(1H-pyrrol-1-ylamino)ethyl]carbamate (4.18 g) was dissolved in 100 ml of methanol and 5% Pd/C (450 mg) was added. The solution was hydrogenated at atmospheric pressure and room temperature until absorption of 90% of the theoretical amount of hydrogen. The catalyst was removed by filtration and the filtrate was evaporated to dryness. The residue was purified by flash column chromatography (silica gel, ethyl acetate/methanol, 19:1) and the desired fractions combined and evaporated. Recrystallization of the residue from ethyl acetate/methanol/hexane afforded the product obtained as a powder (1.24 g), m.p. 147°–148° C.

Analysis: Calculated for $C_9H_{13}N_3O_3$: 51.18%C 6.20%H 19.89%N Found: 50.97%C 6.04%H 19.60%N

EXAMPLE 21

1,1-Dimethylethyl-[4-oxo-4-(1H-pyrrol-1-ylamino)-butyl]carbamate

To a stirred solution consisting of 4-aminobutyric acid (3.0 g) in 50% acetone (aq.) (70 ml) was added triethylamine (6.1 ml) and 2-(tert-butoxycarbonyloxyimino)-2-phenylacetonitrile (7.9 g) at room temperature. After stirring for 21 hours, the reaction mixture was concentrated in vacuo and subsequently diluted with water and ethyl acetate. The layers were separated and the aqueous phase was washed once with ethyl acetate (EtOAc), then acidified to pH 4 using 5% citric acid (aq.). The N-protected amino acid was then extracted three times with EtOAc. The combined organics were washed with brine and dried (MgSO4). Filtration and concentration gave 5.9 g of the desired intermediate as an oil.

To a stirred solution of the N-protected amino acid (5.9 g) and 1-aminopyrrole (2.4 g) in DCM (145 ml) was added DCC (6.1 g) at room temperature. After stirring for 26 hours, the precipitated DCU was removed via filtration and washed with DCM. The combined filtrates were concentrated to give the crude product as an oil which solidified on standing. The solid material was washed several times with heptane and subsequently recrystallized from ether to give 2.5 g of the desired product as a solid, m.p. 141°–143° C.

Analysis: Calculated for $C_{13}H_{21}N_3O_3$: 58.41%C 7.92%H 15.72%N Found: 58.36% C 7.91%H 15.67%N

EXAMPLE 22

4-Amino-N-1H-pyrrol-1-ylbutanamide Fumarate

To a stirred solution of 1,1-dimethylethyl-[4-oxo-4-(1H-pyrrol-1-ylamino)butyl]carbamate (2.3 g), in EtOAc was added ethereal HCl (excess) at room temperature. The reaction mixture was allowed to stir for six days at which time the precipitated product was filtered. The free amine was prepared in ethyl acetate with triethylamine (1.0 equiv) and purified via flash column chromatography (silica gel, 0–100% methanol/ethyl acetate.) The fumarate salt was prepared in absolute ethanol with fumaric acid (0.6 g) and recrystallized from ethanol to give 0.8 g of the desired product as a solid, m.p. 168°–169° C.

Analysis: Calculated for $C_{12}H_{17}N_3O_5$: 50.88%C 6.05%H 14.83%N Found: 50.93%C 6.16%H 14.75%H

EXAMPLE 23

1,1-Dimethylethyl-[3-oxo-3-(1H-pyrrol-1-ylamino)-propyl]carbamate

To a stirred solution consisting of beta-alanine (3.0 g) in 50% acetone (aq.) (90 ml) was added triethylamine (7.0 ml) and 2-(tert-butoxycarbonyloxyimino)-2-phenylacetonitrile (9.1 g) at room temperature. After stirring for 21 hours, the reaction mixture was concentrated in vacuo and subsequently diluted with water and ethyl acetate. The layers were separated and the aqueous phase was washed once with EtOAc, then acidified to pH 4 using 5% citric acid (aq.). The N-protected amino acid was then extracted three times with EtOAc. The combined organics were washed with brine and dried (MgSO4). Filtration and concentration gave 5.5 g of the desired intermediate as an oil which solidified on standing, m.p. 72°–73° C.

To a stirred solution of the N-protected amino acid (5.5 g) and 1-aminopyrrole (2.3 g) in DCM (1 ml) was added DCC (5.8 g) at room temperature. After stirring for 26 hours, the precipitated DCU was removed via filtration and washed with DCM. The combined filtrates were concentrated to give the crude product as an oil which solidified on standing. The solid material was washed several times with heptane and subsequently recrystallized from EtOAc/heptane to give 1.6 g of the desired product as a solid, m.p. 141°–143° C.

Analysis: Calculated for $C_{12}H_{19}N_3O_3$: 56.90% 7.56%H 16.59%N Found: 57.04%C 7.82%H 16.78%N

EXAMPLE 24

1,1-Dimethylethyl-[2-(2-chloro-1H-pyrrol-1-ylamino)-2-oxoethyl]carbamate

To a stirred solution consisting of 1,1-dimethylethyl-[2-oxo-2-(1H-pyrrol-1-ylamino)ethyl]carbamate (8.1 g) and N-chlorosuccinimide (4.9 g) in DMF (60 ml) was added a catalytic amount of AIBN at 40° C. The reaction mixture was stirred for 11 hours at 40° C., cooled to room temperature, and poured into water and ethyl acetate. The layers were separated and the aqueous phase was extracted four times with ethyl acetate. The combined organics were washed twice with water, then brine, and subsequently dried (MgSO4). Filtration and concentration gave the crude product. Purification via flash column chromatography (silica gel, 0–25% EtOAc/heptane) afforded 3.7 g of product as a solid, m.p. 113°–116° C.

Analysis: Calculated for $C_{11}H_{16}ClN_3O_3$: 48.27%C 5.89%H 15.35%N Found: 48.49%C 5.82%H 15.15%N

EXAMPLE 25

2-Amino-N-(2-chloro-1H-pyrrol-1-yl)acetamide Hydrochloride

To a stirred solution of 1,1-dimethylethyl-[2-(2-chloro-1H-pyrrol-1-ylamino)-2-oxoethyl]carbamate (3.1 g) in EtOAc (20 ml) and ether (20 ml) was added ethereal HCl (excess) at room temperature. The reaction mixture was allowed to stir for 19 hours at which time the precipitated product was filtered and washed with EtOAc. Recrystallization from ethanol/ether afforded 0.75 g of the product as a solid, m.p. 220° C. (dec.).

Analysis: Calculated for $C_6H_9Cl_2N_3O$: 34.31%C 4.32%H 20.00%N Found: 34.35%C 3.85%H 19.94%N

EXAMPLE 26

2-(2,5-Dimethyl-1H-pyrrol-1-yl)-1H-isoindole-1,3(2H)dione

A stirred suspension of N-aminophthalimide (19.75 g), acetonylacetone (14.3 ml), p-toluenesulfonic acid (5 mg), and toluene (406 ml) was heated at reflux for 1 hour and cooled to room temperature. The reaction mixture was combined with another reaction mixture and the entire mixture decolorized with activated charcoal. Filtration through a bed of celite gave a solution which upon partial concentration resulted in crystallization of the desired product as a solid (11.0 g), m.p. 182.5°–183.5° C.

Analysis: Calculated for $C_{14}H_{12}N_2O_2$: 69.98%C 5.04%H 11.66%N Found: 69.99%C 4.92%H 11.63%N

EXAMPLE 27(a)

2,5-Dimethyl-1H-pyrrol-1-amine

A stirred mixture of 2-(2,5-dimethyl-1H-pyrrol-1-yl)-1H-isoindole-1,3(2H)dione (9.0 g), anh. hydrazine (7.7 ml), and abs. ethanol (200 ml) was heated at reflux for 3 hours and cooled to room temperature. The reaction was repeated as described above using phthalimide (11.5 g), anh. hydrazine (7.5 ml), and abs. ethanol (150 ml). The precipitated phthalimido by-product from both reaction mixtures was removed by filtration through a bed of celite, and the filtrates combined and concentrated. Purification via flash column chromatography (silica gel, 30% EtOAc/heptane) gave the desired product (6.54 g).

EXAMPLE 27(b)

1,1-Dimethylethyl-[2-(2,5-dimethyl-1H-pyrrol-1-ylamino)-2-oxoethyl]carbamate

To a stirred mixture of 2,5-dimethyl-1H-pyrrol-1-amine (6.54 g), DCM (300 ml) and N-(tert-butoxycarbonyl)glycine (1.40 g), DCC (12.9 g) was added at room temperature. After 16 hours, TLC (silica gel, 50% EtOAc/heptane) indicated the presence of a trace of starting material present. Additional N-(tert-butoxycarbonyl)glycine (3.12 g) and DCC (3.7 g) were added, and stirring continued an additional 2.5 hours. The suspension was filtered, the filtrate was concentrated, and the crude product purified by HPLC (silica gel, 20% EtOAc/DCM, affording 7.89 g of product. Recrystallization from ether/pentane gave the product as a solid, m.p. 87°–88° C.

Analysis: Calculated for $C_{13}H_{21}N_3O_3$: 58.40%C 7.93%H 15.72%N Found: 58.78%C 8.15%H 15.36%N

EXAMPLE 28

2-Amino-N-(2,5-dimethyl-1H-pyrrol-1yl)acetamide Fumarate

A solution of 1,1-dimethylethyl-[2-(2,5-dimethyl-1H-pyrrol-1-ylamino)-2-oxoethyl]carbamate (3.60 g), ether (100 ml), abs. methanol (5 ml) and ethereal HCl (70 ml) was stirred at room temperature under a $N_2$ atmosphere for 3 hours, and stored at 0° C. for 16 hours. The reaction was repeated as above with the BOC-compound (1.6 g), ether (100 ml), methanol (2.5 ml) and ethereal HCl (70 ml). The reaction mixtures were combined, concentrated, and slurried with aqueous bicarbonate and DCM. The layers were separated and the aqueous layer extracted 5 times with DCM. The combined organic layers were dried ($K_2CO_3$), filtered, and concentrated. Purification via flash column chromatography (silica gel, 5–20% methanol/DCM gave the desired amine product (2.18 g).

The amine (2.02 g) was dissolved in abs. ethanol (30 ml) and added to a hot solution consisting of fumaric acid (1.39 g.) and abs. ethanol (25 ml). The resulting salt precipitated out of solution and was collected by filtration. Recrystallization from methanol/ether gave a salt with 0.635 equivalents fumaric acid, m.p. 198°–200° C.

Analysis: Calculated for $C_8H_{13}N_3O \cdot 0.635\ C_4H_4O_4$ 52.53%C 6.51%H 17.44%N Found: 52.21%C 6.54%H 16.99%N

EXAMPLE 29

2-Amino-N-(2,5-dichloro-1H-pyrrol-1-yl)acetamide Hydrochloride

To a stirred solution of 2-amino-N-1H-pyrrol-1-ylacetamide (8.1 g) and N-chlorosuccinimide (NCS) (4.9 g) in DMF (60 ml) was added a catalytic amount of AIBN at 40° C. The reaction mixture was stirred for 11 hours, cooled to room temperature, and poured into water. The product was extracted 4 times into EtOAc, washed with water, then brine, and subsequently dried (MgSO$_4$). Filtration and concentration gave the crude product which was purified via flash column chromatography (silica gel, 0–25% EtOAc/heptane). A solution of the product and EtOAc (15 ml) was treated with ethereal HCl (excess). The precipitate was filtered and recrystallized from methanol/EtOAc to give 0.72 g of the product as a solid, m.p. 225° C. (dec.).

Analysis: Calculated for $C_6H_8Cl_3N_3O$: 29.47%C 3.30%H 17.19%N Found: 29.90%C 3.25%H 17.34%N

EXAMPLE 30

2-(2-Phenyl-1H-pyrrol-1-yl)-1H-isoindole-1,3(2H)-dione

To a stirred suspension of 4-oxo-4-phenyl-1-butanal (6.9 g) in toluene (400 ml) was added 1-aminophthalimide (6.9 g) and a catalytic amount of p-toluenesulfonic acid at room temperature. The reaction mixture was warmed to reflux (1.5 hours) and the water was removed via a Dean-Stark trap. After cooling to room temperature, the reaction mixture was concentrated to dryness and purified via flash column chromatography (silica gel, DCM) to afford 8.3 g of the product as a solid, m.p. 168°–170° C.

Analysis: Calculated for $C_{18}H_{12}N_2O_2$: 74.99%C 4.20%H 9.72%N Found: 75.24%C 4.12%H 9.72%N

EXAMPLE 31

2-Phenyl-1H-pyrrol-1-amine

To a stirred suspension consisting of 2-(2-phenyl-1H-pyrrol-1-yl)-1H-isoindol-1,3(2H)dione (7.2 g) in abs. ethanol (150 ml) was added hydrazine (3.9 ml) at room temperature. The reaction mixture was warmed to reflux for 2 hours and allowed to cool to room temperature overnight. The solid by-product was filtered and washed with ether. The combined filtrates were concentrated in vacuo to give an oil which solidified on standing. Recrystallization from ether afforded 3.9 g of the product as a solid, m.p. 80°–82° C.

Analysis: Calculated for $C_{10}H_{10}N_2$: 75.92%C 6.37%H 17.71%N Found: 75.68%C 6.25%H 17.50%N

EXAMPLE 32

1,1-Dimethylethyl-[2-(2-phenyl-1H-pyrrol-1-ylamino)-2-oxoethyl]carbamate

To a stirred solution consisting of 2-phenyl-1H-pyrrol-1-amine (3.0 g) and N-(tert-butoxycarbonyl)glycine (3.5 g) in DCM (95 ml) was added DCC (4.3 g) at room temperature. The reaction mixture was stirred for 22 hours at which time the precipitated DCU was filtered and washed with DCM. The combined filtrates were concentrated to give the crude product. Purification via flash column chromatography (silica gel, DCM, then 50% EtOAc/heptane) and concentration of the appropriate fractions afforded the product as a foam which was crystallized from ether/heptane to give 2.8 g of the product as a solid, m.p. 136°–138° C.

Analysis: Calculated for $C_{17}H_{21}N_3O_3$: 64.74%C 6.71%H 13.33%N Found: 64.91%C 6.84%H 13.01%N

EXAMPLE 33

2-[2-(1H-Pyrrol-2-ylcarbonyl)-1H-pyrrol-1-yl]-1H-isoindole-1,3(2H)dione

To a suspension of pyrrole-2-carboxylic acid (5.55 g) in 500 ml of DCM was added oxalyl chloride (8.7). The reaction mixture was heated under reflux for 1 hour, cooled to −10° C., and tin (IV) chloride (5.85 ml) was added. After stirring the mixture at −10° C. for 30 minutes, 2-(1H-pyrrol-1-yl)-1H-isoindole-1,3(2H)dione (10.6 g) was added in four portions over a period of 30 minutes, followed by stirring at −10° C. for additional 30 minutes. The reaction mixture was then poured into 500 ml of water and extracted with DCM. The combined extracts were washed with 1N sodium hydroxide solution, 1N sulfuric acid, and finally with water. The dried (magnesium sulfate) organic phase was filtered and evaporated in vacuo. The residue was triturated with DCM, affording the product as a powder (10.55 g), mp 204°–206° C.

Analysis: Calculated for $C_{17}H_{11}N_3O_3$: 66.88%C 3.63%H 13.76%N Found: 66.33%C 3.49%H 13.49%N

EXAMPLE 34

(1H-Amino-1H-pyrrol-2-yl)-1H-pyrrol-2-ylmethanone

To a solution of 2-[2-(1H-pyrrol-2-ylcarbonyl)-1H-pyrrol-1-yl]-1H-isoindole-1,3(2H)dione (13.46 g) in 100 ml of dimethylformamide was added 45 ml of an aqueous 40% methylamine solution. After stirring for 2 hours at room temperature, the reaction mixture was diluted with 500 ml of water and extracted with DCM. The combined extracts were washed with water, dried over magnesium sulfate and evaporated in vacuo. The residue was recrystallized from DCM/ethyl acetate/hexane affording the product as pale beige crystals (5.68 g), m.p. 145°–148° C.

Analysis: Calculated for $C_9H_9N_3O$: 61.70%C 5.18%H 23.99%N Found: 61.61%C 5.08%H 23.70%N

EXAMPLE 35

Phenylmethyl-[2-oxo-2-[[2-(1H-pyrrol-2-ylcarbonyl)-1H-pyrrol-1-yl]amino]ethyl]carbamate To a solution of (1-amino-1H-pyrrol-2-yl)-1H-pyrrol-2-ylmethanone (4.41 g) and N-carbobenzyloxyaminoglycine (5.27 g) in 10 ml of anhydrous dimethylformamide and 100 ml of anhydrous DCM was added DCC (6.23 g). The reaction mixture was stirred overnight at room temperature, filtered and the filtrate evaporated in vacuo. The residual oil was purified by preparative HPLC (n-heptane/ethyl acetate 2:3) and subsequent recrystallization from ethyl acetate/n-heptane afforded the product as a powder (6.74 g), m.p. 157°–158° C.

Analysis: Calculated for $C_{19}H_{18}N_4O_4$: 62.29%C 4.95%H 15.29%N Found: 62.21%C 4.94%H 15.17%N

EXAMPLE 36

2-Amino-N-[2-(1H-pyrrol-2-ylcarbonyl)-1H-pyrrol-1-yl]acetamide Hydrochloride

Phenylmethyl-[2-oxo-2-[[2-(1H-pyrrol-2-ylcarbonyl)-1H-pyrrol-1-yl]amino]ethyl]carbamate (5.33 g) was hydrogenated as a solution in 100 ml of methanol over 5% Pd/C (500 mg) at room temperature and atmospheric pressure overnight. The reaction mixture was diluted with methanol, filtered and evaporated in vacuo, The residue was dissolved in 100 ml of methanol and 400 ml of ethyl ether and reacted with 12 ml of 1.25M ethereal hydrogen chloride solution. The precipitate was recrystallized from methanol/ethyl ether affording 2.24 g of the product as a powder, m.p. 238°–246° C. (dec.).

Analysis: Calculated for $C_{11}H_{13}ClN_4O_2$: 49.17%C 4.88%H 20.85%N Found: 48.89%C 5.10%H 20.36%N Following a procedure similar to that described in Example 36, using 5% or 10% Pd/C, the following 2-amino-N-[2-(substituted benzoyl)-1H-pyrrol-1-yl]acetamides were prepared:

TABLE I

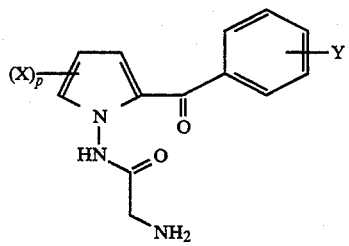

| Ex | X | Y | m.p. (°C.) | Salt |
|---|---|---|---|---|
| 68 | H | 4-F | 235 (dec.) | HCl |
| 72 | H | 3-F | 161–163 | fumarate |
| 76 | H | 2-CH$_3$ | 166–169 | maleate |
| 80 | H | 4-OCH$_3$ | 215 (dec.) | HCl |
| 82 | H | 2-OCH$_3$ | 188 (dec.) | HCl |
| 86 | H | 2-CF$_3$ | 120–122 | HBr |

EXAMPLE 37

2-[2-(2-Thienylcarbonyl)-1H-pyrrol-1-yl]-1H-isoindole-1,3(2H) dione

A solution of 2-thiophenecarbonylchloride (10.7 ml) in 500 ml of dry DCM was treated at −10° C. with tin tetrachloride (11.7 ml) and stirred for 30 minutes. 2-(1H-pyrrol-1-yl)-1H-isoindole-1,3(2H)dione (21.2 g) was then added in small portions over a period of 30 minutes at −10° C. After the addition was completed, the reaction mixture was stirred for an additional 30 minutes at −10° C. and subsequently poured into 500 ml of ice water. The precipitate was dissolved by addition of about 1000 ml of DCM and the separated aqueous layer extracted again with DCM. The combined organic layers were washed twice with 2N hydrochloric acid and with water, dried over magnesium sulfate and evaporated in vacuo. The residue was purified by flash column chromatography (silica gel, DCM/ethyl acetate 99:1) and the desired fractions were concentrated. The residue was recrystallized from DCM/ethyl ether affording the product as crystals (17.9 g), m.p. 165°–166° C.

Analysis: Calculated for $C_{17}H_{10}N_2O_3S$: 63.35%C 3.13%H 8.69%N Found: 63.07%C 3.17%H 8.65%N

EXAMPLE 38

(1-Amino-1H-pyrrol-2-yl)-2-thienylmethanone

To a solution of 2-[2-(2-thienylcarbonyl)-1H-pyrrol-1-yl]-1H-isoindole-1,3(2H)dione (15.43 g) in 50 ml of dimethylformamide was added 50 ml of 40% methylamine. The reaction mixture was stirred for 1.5 hours at room temperature, diluted with water and extracted with DCM. The combined organic layers were washed with water, dried over magnesium sulfate and evaporated in vacuo. The residual oil was recrystallized from ethyl ether/hexane to afford the product (5.96 g), m.p. 81°–82° C.

Analysis: Calculated for $C_9H_8N_2OS$: 56.23%C 4.19%H 14.57%N Found: 56.56%C 4.00%H 14.57%N

EXAMPLE 39

1,1-Dimethylethyl-[2-oxo-2-[[2-(2-thienylcarbonyl)-1H-pyrrol-1-yl]amino]ethyl]carbamate (1-Amino-1H-pyrrol-2-yl)-2-thienylmethanone (6.79 g) and N-tert-butoxycarbonylglycine (6.19 g) were dissolved in 100 ml of dry DCM and reacted with DCC (9.40 g). The reaction mixture was stirred at room temperature overnight and then filtered. The filtrate was evaporated in vacuo, dissolved in about 200 ml of ethyl ether and again filtered. The filtrate was evaporated in vacuo and the residual oil was purified by flash column chromatography (silica gel, DCM/ethyl acetate 5:1) followed by recrystallization from DCM/ethyl ether to afford the product as needles (8.65 g), m.p. 115°–116° C.

Analysis: Calculated for $C_{16}H_{19}N_3O_4S$: 55.00%C 5.48%H 12.03%N Found: 55.44%C 5.62%H 12.00%N Following a procedure similar to that described in Example 39, the following 1,1-dimethylethyl-[2-[[2-(substituted-benzoyl)-1H-pyrrol-1-yl]amino]-2-oxoethyl]carbamates were prepared:

TABLE II

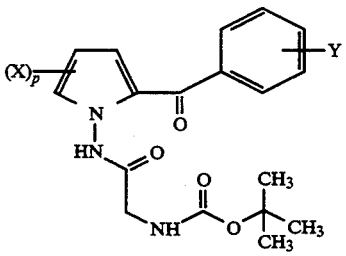

| Ex | X | Y | m.p. (°C.) |
|---|---|---|---|
| 61 | H | 2-F | 114–116 |
| 90 | 5-Cl | 2-F | 148–150 |

EXAMPLE 40

2-Amino-N-[2-(2-thienylcarbonyl)-1H-pyrrol-1-yl]acetamide Hydrochloride

To a solution of 1,1-dimethylethyl-[2-oxo-2-[[2-(2-thienylcarbonyl)-1H-pyrrol-1-yl]amino]ethyl]carbamate (6.20 g) in 200 ml of dry ethyl ether was added 80 ml of a 3.5M ethereal hydrogen chloride solution. The reaction mixture was stirred at room temperature for 7 days. The precipitate was collected by suction filtration, dissolved in 50 ml of hot isopropanol and evaporated in vacuo. The residual oil was crystallized from isopropanol/ethyl ether affording the product as crystals (2.61 g), m.p. 168°–169° C.

Analysis: Calculated for $C_{11}H_{12}ClN_3O_2S$: 46.24%C 4.23%H 14.70%N Found: 46.13%C 3.96%H 14.73%N Following a procedure similar to that described in Example 40, using an appropriate acid, the following 2-amino-N-[2-(substituted benzoyl)-1H-pyrrol-1-yl]acetamides were prepared.

TABLE III

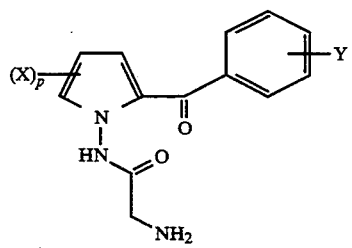

| Ex | X | Y | m.p. (°C.) | Salt/Hydrate |
|---|---|---|---|---|
| 58 | H | 2-Cl | 165–167 | HCl |
| 62 | H | 2-F | 121–125 | HBr hemihydrate |
| 91 | 5-Cl | 2-F | 135–139 | HBr hemihydrate |

EXAMPLE 41

2-[2-[(3-Methyl-2-thienyl)carbonyl]-1H-pyrrol-1-yl]-1H-isoindole-1,3(2H)dione

To a stirred solution consisting of 3-methyl-2-thiophenecarboxylic acid (21.0 g) in dry DCM (1.5 l) was added oxalyl chloride (21.0 ml) at room temperature under nitrogen. After stirring for 1 hour at room temperature, the reaction mixture was cooled to −10° C. and tin (IV) chloride (17.3 ml) was added. The resulting solution was stirred for 10 minutes (−10° C.) at which time 2-(1H-pyrrol-1-yl)-1H-isoindole-1,3(2H)dione (31.3 g) was added in three portions. After stirring for 1 hour in the cooling bath, the reaction mixture was poured into cold water and the layers separated. The organic phase was washed twice with 5% HCl (aq.) and dried (MgSO₄). Filtration and concentration gave the crude product. Purification via preparative HPLC (silica gel, DCM) afforded 12.5 g of the product as a solid, m.p. 221°–223° C.

Analysis: Calculated for $C_{18}H_{12}N_2O_3S$: 64.27%C 3.60%H 8.33%N Found: 64.37%C 3.64%H 8.26%N

EXAMPLE 42

(1-Amino-1H-pyrrol-2-yl)-(3-methyl-2-thienyl)methanone

To a solution consisting of 2-[2-[(3-methyl-2-thienyl)carbonyl]-1H-pyrrol-1-yl]-1H-isoindole-1,3(2H)dione (11.5 g) in DMF (30 ml) was added 40% methylamine (aq., 34.0 ml) solution at room temperature. The reaction mixture was stirred at ambient temperature for 3.5 hours, then poured into water and ethyl acetate. The layers were separated and the aqueous phase was extracted thrice with EtOAc. The combined organics were washed with water, brine, and dried (MgSO₄). Filtration and concentration gave the crude product. Purification via preparative HPLC (silica gel, 2:1 heptane/EtOAc), followed by crystallization from ether/pentane afforded 5.6 g of the product as a solid, m.p. 42°–44° C.

Analysis: Calculated for $C_{10}H_{10}N_2OS$: 58.23%C 4.89%H 13.58%N Found: 58.35%C 4.82%H 13.35%N

EXAMPLE 43

1,1-Dimethylethyl-[2-oxo-2-[[2-(3-methyl-2-thienylcarbonyl)-1H-pyrrol-1-yl]amino]ethyl]carbamate To a stirred solution consisting of (1-amino-1H-pyrrol-2-yl)-(3-methyl-2-thienyl)methanone (1.0 g) and N-(tert-butoxycarbonyl)glycine (0.85 g) in dry DCM (24 ml) was added DCC (1.0 g) at room temperature. The reaction mixture was stirred for 2 hours and filtered. The solid DCU was washed with DCM and the combined filtrates were concentrated to give the crude product as an oil. On dilution with EtOAc/hexane, the product solidified. Recrystallization from EtOAc/hexane gave 1.05 g of the product as a solid, m.p. 115°–116° C.

Analysis: Calculated for $C_{17}H_{21}N_3O_4S$: 56.18%C 5.82%H 11.56%N Found: 56.38%C 5.87%H 11.47%N

EXAMPLE 44

2-(2-Acetyl-1H-pyrrol-1-yl)-1H-isoindole-1,3(2H)dione

To a stirred solution of acetyl chloride (6.77 ml) in DCM (400 ml) was added tin (IV) chloride (11.14 ml) at −5° C., under nitrogen. 2-(1H-pyrrol-1-yl)-1H-isoindole-1,3(2H)dione (20.0 g) was then added portionwise, keeping the temperature below 0° C. The reaction mixture was then stirred at 0° C. for 0.5 hour, at which time it was poured into ice water. The layers were separated and the aqueous phase was extracted with DCM. The combined organics were washed twice with 5% HCl (aq.) and dried (MgSO$_4$). Filtration and concentration gave the crude product. Purification via flash column chromatography (silica gel, DCM) afforded 9.62 g of the product as a solid, m.p. 204°–205° C.

Analysis: Calculated for $C_{14}H_{10}N_2O_3$: 66.14%C 3.96%H 11.02%N Found: 65.95%C 3.96%H 10.98%N Following a procedure similar to that described in Example 44, using an appropriate acyl chloride, the following 2-[2-(substituted benzoyl)-1H-pyrrol-1-yl]-1H-isoindole-1,3(2H)diones were prepared:

TABLE IV

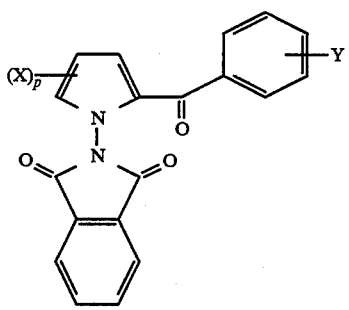

| EX | X | Y | m.p. (°C.) |
|---|---|---|---|
| 56 | H | 2-Cl | 162–163 |
| 59 | H | 2-F | 206–208 |
| 65 | H | 4-F | 155-157 |
| 69 | H | 3-F | 136–139 |
| 73 | H | 2-CH$_3$ | 149–151 |
| 77 | H | 4-OCH$_3$ | 195–198 |
| 81 | H | 2-OCH$_3$ | 189–191 |
| 83 | H | 2-CF$_3$ | 164–165 |
| 88 | 5-Cl | 2-F | 198–200 (dec.) |

EXAMPLE 45

1-(1-Amino-1H-pyrrol-2-yl)ethanone

To a suspension of 2-(2-acetyl-1H-pyrrol-1-yl)-1H-isoindole-1,3(2H)dione (8.53 g) in dimethylformamide (25 ml) was added 33 ml of 40% methylamine solution. After 2.5 hours, the reaction mixture was poured into water (300 ml) and was extracted 4 times with EtOAc. The combined organics were washed once with water and brine, dried (MgSO$_4$), filtered and concentrated to give the crude product. Purification via flash column chromatography (silica gel, 30% EtOAc/hexane) afforded 3.88 g of the product as an oil.

Following a procedure similar to that described in Example 45, the following (1-amino-1H-pyrrol-2-yl)substituted-phenylmethanones were prepared:

TABLE V

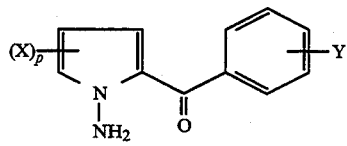

| Ex. | X | Y | m.p. (°C.) |
|---|---|---|---|
| 57 | H | 2-Cl | 161–163 |
| 60 | H | 2-F | 44–46 |
| 66 | H | 4-F | 94–95 |
| 70 | H | 3-F | 54–57 |
| 74 | H | 2-CH$_3$ | 79–82 |
| 78 | H | 4-OCH$_3$ | 90–91 |
| 84 | H | 2-CF$_3$ | 58–60 |
| 89 | 5-Cl | 2-F | 85–87 |

EXAMPLE 46

Phenylmethyl-[2-[(2-acetyl-1H-pyrrol-1-yl)amino]-2-oxoethyl]carbamate

To a stirred solution consisting of 1-(1-amino-1H-pyrrol-2-yl)ethanone (3.88 g) and carbobenzyloxyglycine (6.54 g) in dry DCM (115 ml) was added DCC (6.77 g) at 0° C. under nitrogen. The reaction mixture was allowed to stir at room temperature for 18 hours. The precipitated DCU was removed by filtration and washed with ethyl acetate. The combined filtrates were concentrated to give the crude product. Purification via flash column chromatography (silica gel, 10% EtOAc/hexane) afforded 6.98 g of the product as a solid, m.p. 109°–111° C.

Analysis: Calculated for $C_{16}H_{17}N_3O_4$: 60.94%C 5.43%H 13.33%N Found: 61.19%C 5.37%H 13.16%N Following a procedure similar to that described in Example 46, the following phenylmethyl-[2-[(substituted-benzoyl-1H-pyrrol-1-yl)amino]-2-oxoethyl]carbamates were prepared;

TABLE VI

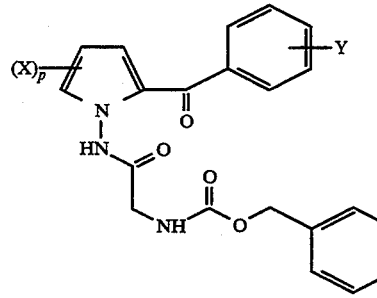

| Ex | X | Y | m.p. (°C.) |
|---|---|---|---|
| 67 | H | 4-F | 115–117 |
| 71 | H | 3-F | 113–115 |
| 75 | H | 2-CH$_3$ | 92–94 |
| 79 | H | 4-OCH$_3$ | 125–127 |
| 85 | H | 2-CF$_3$ | 105–107 |

EXAMPLE 47

1,1-Dimethylethyl-[2-[(2-acetyl-1H-pyrrol-1-yl)amino]-2-oxoethyl]carbamate

To a stirred solution consisting of 1-(1-amino-1H-pyrrol-2-yl)ethanone (3.51 g) and N-(tert-butoxycarbonyl)glycine (4.96 g) in dry DCM (114 ml) was added DCC (5.90 g) at room temperature. The reaction mixture was stirred for one hour, and then filtered. The DCU filter cake was washed with DCM and the combined filtrates were concentrated to give the crude product as a solid. The product was suspended in 70% EtOAc/hexane and filtered. The filter cake was dissolved in DCM and a small amount of insoluble DCU was removed by filtration. Concentration of the filtrate afforded 7.04 g of the product as a solid, m.p. 158°–159° C.

Analysis: Calculated for $C_{13}H_{19}N_3O_4$: 55.51%C 6.81%H 14.94%N Found: 55.73%C 6.90%H 14.81%N

EXAMPLE 48

N-(2-Acetyl-1H-pyrrol-1-yl)-2-aminoacetamide Hydrochloride

To a stirred solution consisting of 1,1-dimethylethyl-[2-[(2-acetyl-1H-pyrrol-1-yl)-amino]-2-oxoethyl]carbamate (5.90 g) in ethyl acetate (45 ml) and isopropanol (35 ml) was added ethereal HCl (1.7M, excess). The resulting suspension was gently heated until the reaction mixture was homogeneous. After stirring for 24 hours at room temperature, the reaction appeared complete by TLC (silica gel, 50% EtOAc/hexane). The solid product was collected by filtration under nitrogen and recrystallized from methanol/ether to afford 3.30 g of the product, m.p. 179°–182° C.

Analysis: Calculated for $C_8H_{12}ClN_3O_2$: 44.15%C 5.56%H 19.31%N Found: 44.17%C 5.61%H 19.27%N

EXAMPLE 49

2-[2-(2-Methyl-1-oxopropyl)-1H-pyrrol-1-yl]-1H-isoindole-1,3(2H)dione

To a stirred solution of isobutyryl chloride (5.4 ml) in DCM (250 ml) was added tin (IV) chloride (5.8 ml) at −10° C. under nitrogen. After stirring for 15 minutes in the cooling bath, 2-(1H-pyrrol-1-yl)-1H-isoindole-1,3(2H)dione (10.0 g) was added portion-wise. The reaction mixture was allowed to warm to room temperature, and stir for three days, at which time it was poured into cold water. The layers were separated and the organic phase was washed twice with water, once with 5% HCl (aq.), and subsequently dried (MgSO4). Filtration and concentration gave the crude product. Purification via preparative HPLC (silica gel, DCM) afforded 2.5 g of the product as a solid, m.p. 147°–149° C.

Analysis: Calculated for $C_{16}H_{14}N_2O_3$: 68.08%C 5.00%H 9.92%N Found: 67.65%C 4.98%H 9.93%N

EXAMPLE 50

1-(1-Amino-1H-pyrrol-2-yl)-2-methyl-1-propanone Hydrochloride

To a solution consisting of 2-[2-(2-methyl-1-oxopropyl)-1H-pyrrol-1-yl]-1H-isoindole-1,3(2H)dione (14.5 g) in DMF (50 ml) was added 40% methylamine (aq.) (51.0 ml) at room temperature. The reaction mixture was stirred at ambient temperature for 4 hours at which time it was poured into water and ethyl acetate. The layers were separated and the aqueous phase was extracted three times with EtOAc. The combined organics were washed with water, then brine, and subsequently dried (MgSO4). Filtration and concentration gave the crude product. Purification via HPLC (silica gel, 3:1 heptane/EtOAc) afforded 7.5 g of the desired product as an oil. The hydrochloride salt was prepared in ethyl acetate (40 ml) with ethereal HCl and sublimed at 80° C. to give the product as a solid, m.p. 93°–94° C.

Analysis: Calculated for $C_8H_{13}ClN_2O$: 50.93%C 6.95%H 14.85%N Found: 51.11%C 6.73%H 14.89%N

EXAMPLE 51

1,1-Dimethylethyl-[2-[[2-(2-methyl-1-oxopropyl)-1H-pyrrol-1-yl]amino]-2-oxoethyl]carbamate To a stirred solution consisting of 1-(1-amino-1H-pyrrol-2-yl)-2-methyl-1-propanone (0.8 g) and N-(tert-butoxycarbonyl)glycine (0.9 g) in DCM (25 ml) was added DCC (1.1 g) at room temperature. The reaction mixture was stirred for 2 hours at which time the precipitated DCU was filtered and washed with DCM. The combined filtrates were concentrated to give the crude product as an oil which was diluted with ether to precipitate any residual DCU. After removing the DCU via filtration, the filtrate was diluted with pentane to precipitate the product (1.0 g) as a solid, m.p. 104°–106° C.

Analysis: Calculated for $C_{15}H_{23}N_3O_4$: 58.24%C 7.49%H 13.58%N Found: 58.30%C 7.57%H 13.44%N

EXAMPLE 52

2-Amino-N-[2-(2-methyl-1-oxopropyl)-1H-pyrrol-1-yl]acetamide Hydrochloride

To a stirred solution of 1,1-dimethylethyl-[2-[[2-(1-(2-methyl-1-oxo)propyl-1H-pyrrol-1-yl]amino]-2-oxoethyl]carbamate (5.6 g) in acetone (55 ml) was added ethereal HCl (excess) at room temperature. The reaction mixture was allowed to stir for 18.5 hours at which time the precipitated product (2.5 g) was filtered and washed with acetone, m.p. 168°–171° C.

Analysis: Calculated for $C_{10}H_{16}ClN_3O_2$: 48.88%C 6.56%H 17.10%N Found: 48.95%C 6.66%H 17.01%N

EXAMPLE 53

3-Benzoylpyrrole*

To a stirred suspension of sodium hydride (8.0 g) in 200 ml of dry ethyl ether was added dropwise a solution of phenylvinylketone (13.22 g) and tosylmethyl isocyanide (19.52) in 150 ml of dry methyl sulfoxide and 300 ml of dry ethyl ether at such a rate that the ether refluxed gently. After complete addition, the suspension was stirred at room temperature for 30 minutes and subsequently hydrolyzed by dropwise addition of 200 ml of water. The ether layer was separated and the aqueous layer extracted with ethyl acetate. The combined organic layers were washed with water, 0.1N sulfuric acid, and again with water. The organic phase was dried over magnesium sulfate, filtered and evaporated in vacuo. The residue was purified by flash column chromatography (silica gel, DCM/ethyl acetate, 5:1). The desired fractions were concentrated and the residual oil was crystallized from DCM/hexane, affording the product as crystals (7.11 g), m.p. 98°–99° C. (lit*m.p. 96°–97° C.).

*J. Rokach, P. Hamel and M. Kakushima, Tetrahedron Lett., 22, 4901–4904 (1981).

Analysis: Calculated for $C_{11}H_9NO$: 77.17%C 5.30%H 8.18%N Found: 76.86%C 5.41%H 8.01%N

EXAMPLE 54

(1-Amino-1H-pyrrol-3-yl)phenylmethanone

To a solution of 3-benzoylpyrrole (4.92 g) in 50 ml of dry dimethylformamide was added milled potassium hydroxide (8.06 g). Hydroxylamine-O-sulfonic acid (4.23 g) was added to the suspension in 4 portions over a period of 1 hour with stirring at room temperature. After the addition was completed the reaction mixture was stirred for 30 minutes at room temperature, and subsequently diluted with 50 ml of water and extracted with DCM. The combined organic layers were washed with water, dried over magnesium sulfate and evaporated in vacuo. The residue was purified by flash column chromatography (silica gel, DCM/ethyl acetate, 5:1), affording starting material (1.44 g) and the desired product as the second fraction. Recrystallization from ethyl ether/hexane gave the product as crystals (1.80 g), which was combined with material obtained from a 36.9 mmol scale reaction and recrystallized from DCM/hexane affording 3.20 g of crystals, m.p. 82°–83° C.

Analysis: Calculated for $C_{11}H_{10}N_2O$: 70.95%C 5.41%H 15.04%N Found: 70.65%C 5.49%H 14.97%N

EXAMPLE 55

Phenylmethyl-[2-[(3-benzoyl-1H-pyrrol-1-yl)amino]-2-oxoethyl]carbamate

To a solution of (1-amino-1H-pyrrol-3-yl)phenylmethanone (5.96 g) and N-carbobenzyloxyglycine (6.69 g) in 70 ml of anhydrous DCM and 30 ml of anhydrous dimethylformamide was added DCC (7.22 g). The reaction mixture was stirred at room temperature for 4 hours and filtered. The filter cake was washed with ethyl acetate, and the combined filtrates were evaporated in vacuo. The residual oil was purified by preparative HPLC (silica gel, DCM/ethyl acetate 3:1). Evaporation of the desired fractions afforded a colorless oil, which was crystallized from DCM/ethyl ether yielding the product as colorless crystals (5.96 g), m.p. 144°–145° C.

Analysis: Calculated for $C_{21}H_{19}N_3O_4$: 66.83%C 5.07%H 11.13%N Found: 67.18%C 5.10%H 11.21%N

EXAMPLE 63

2-(Acetylamino-N-[2-(2-fluorobenzoyl)-1H-pyrrol-1-yl]acetamide

To a solution of 2-amino-N-[2-(2-fluorobenzoyl)-1H-pyrrol-1-yl]acetamide hydrobromide hemihydrate (2.09 g) in 10 ml of anhydrous dimethylformamide and 40 ml of anhydrous DCM were added pyridine (1.89 g) and acetic anhydride (1.22 g). The reaction mixture was stirred at room temperature for 1 hour, subsequently diluted with water and extracted with DCM. The combined organic layers were washed with 5% hydrochloric acid and water, dried over magnesium sulfate and evaporated in vacuo. The residual oil was recrystallized from DCM/ethyl ether affording the product as crystals (1.58 g), m.p. 146°–147° C.

Analysis: Calculated for $C_{15}H_{14}FN_3O_3$: 59.40%C 4.65%H 13.85%N Found: 59.09%C 4.44%H 13.67%N

EXAMPLE 64

N-[2-(2-Fluorobenzoyl)-1H-pyrrol-1-yl]-2-(methylamino)acetamide Hydrobromide

To a solution of (1-amino-1H-pyrrol-2-yl)-(2-fluorophenyl)methanone (3.46 g) and N-tert-butoxycarbonyl-N-methylglycine (3.21 g) in 100 ml of anhydrous DCM was added DCC (4.20 g). The reaction mixture was stirred overnight at room temperature. The suspension was filtered and the filtrate evaporated in vacuo. Purification of the residue by preparative HPLC (heptane/ethyl acetate, 50:50) afforded the BOC-protected intermediate as an oil (4.26 g). The oil was dissolved in 10 ml of ethyl acetate and 40 ml of ethyl ether, and reacted with 18 ml of a 1.05M ethereal hydrogen bromide solution. After stirring for 2 hours at room temperature, the product was collected as a powder (3.42 g), m.p. 145°–146° C.

Analysis: Calculated for $C_{14}H_{15}BrFN_3O_2$: 47.21%C 4.24%H 11.80%N Found: 46.89%C 4.08%H 11.69%N

EXAMPLE 87

2-(2-Chloro-1H-pyrrol-1-yl)-1H-isoindole-1,3(2H)dione

To a stirred solution consisting of 2-(1H-pyrrol-1-yl)-1H-isoindole-1,3(2H)dione (25.0 g) and N-chlorosuccinimide (14.2 g) in DMF (degassed, 900 ml) was added 2,2'-azobisisobutyronitrile. The reaction mixture was warmed to 40° C. for one hour. Upon cooling to room temperature, the reaction mixture was poured into water and ethyl acetate. The layers were separated and the aqueous phase was extracted thrice with ethyl acetate. The combined organic layers were washed once with water, then brine, and subsequently dried (MgSO$_4$). Filtration and concentration gave the crude product. Purification via preparative HPLC (silica gel, 15% EtOAc/hexane) afforded 14.4 g of the product as a solid, m.p. 130°–132° C.

Analysis: Calculated for $C_{12}H_7ClN_2O_2$: 58.44%C 2.86%H 11.36%N Found: 58.47%C 2.89%H 11.26%N

We claim:

1. A compound of the formula

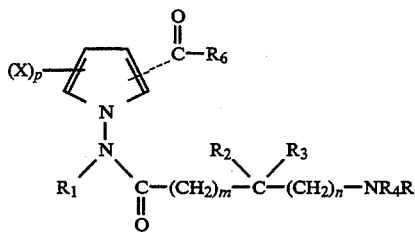

wherein $R_1$ is hydrogen or loweralkyl;

$R_2$ is hydrogen, loweralkyl, hydroxyloweralkyl, acyloxyloweralkyl or loweralkoxyloweralkyl;

$R_3$ is hydrogen or loweralkyl;

or $R_2$ and $R_3$ taken together form a cycloalkyl ring of 3 to 7 carbon atoms;

$R_4$ is hydrogen, loweralkyl, aryl or arylloweralkyl;

$R_5$ is hydrogen, loweralkyl, acyl, aryloxycarbonyl, loweralkoxycarbonyl, or arylloweralkoxycarbonyl;

X is hydrogen, halogen, cyanoloweralkyl, aryl, arylloweralkyl, hydroxyloweralkyl, arylhydroxyloweralkyl, aminoloweralkyl, loweralkylaminoloweralkyl, diloweralkylaminoloweralkyl, arylsulfonyl, loweralkylsulfonyl;

m and n are independently 0 to 5 with the proviso that the sum of m and n does not exceed 5;

p is 0, 1 or 2; and when the dotted line between the pyrrole ring and the carbonyl group represents a bond, R₆ is hydrogen, loweralkyl, hydroxy, loweralkoxy, amino, loweralkylamino, diloweralkylamino,

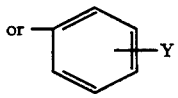

where Y is loweralkoxy, hydroxy, or heteroaryl selected from

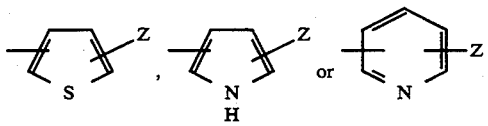

where Z is hydrogen, halogen or loweralkyl;

or a pharmaceutically acceptable acid addition salt thereof, or where applicable a optical or geometrical isomer or racemic mixture thereof.

2. A compound as defined in claim 1 wherein R₆ is loweralkyl.

3. A compound as defined in claim 1 wherein R₆ is

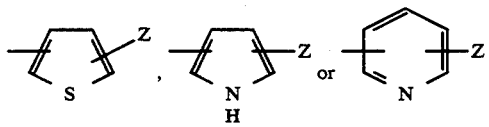

where Z is hydrogen, halogen or loweralkyl.

4. The compound as defined in claim 1 which is 1-amino-N-1H-pyrrol-1-ylcyclopropanecarboxamide.

5. The compound as defined in claim 1 which is 1,1-dimethylethyl-[1-[(1H-pyrrol-1-ylamino)carbonyl]cyclopropyl]carbamate.

6. The compound as defined in claim 1 which is 1,1-dimethylethyl-[2-oxo-2-(1H-pyrrol-1-ylamino)ethyl]carbamate.

7. The compound as defined in claim 1 which is phenylmethyl-[2-oxo-2-(1H-pyrrol-1-ylamino)ethyl]carbamate.

8. The compound as defined in claim 1 which is 1,1-dimethylethyl-[1-[(1H-pyrrol-1-ylamino)carbonyl]cyclopentyl]carbamate.

9. The compound as defined in claim 1 which is 1-amino-N-1H-pyrrol-1-ylcyclopentanecarboxamide.

10. The compound as defined in claim 1 which is (±)-1,1-dimethylethyl-[1-methyl-2-oxo-2-(1H-pyrrol-1-ylamino)ethyl]carbamate.

11. The compound as defined in claim 1 which is (±)-phenylmethyl-[1-methyl-2-oxo-2-(1H-pyrrol-1-ylamino)ethyl]carbamate.

12. The compound as defined in claim 1 which is (R)-phenylmethyl-[1-methyl-2-oxo-2-(1H-pyrrol-1-ylamino)ethyl]carbamate.

13. The compound as defined in claim 1 which is (S)-phenylmethyl-[1-methyl-2-oxo-2-(1H-pyrrol-1-ylamino)ethyl]carbamate.

14. The compound as defined in claim 1 which is (S)-phenylmethyl-[1-(hydroxymethyl)-2-oxo-2-(1H-pyrrol-1-ylamino)ethyl]carbamate.

15. The compound as defined in claim 1 which is (S)-2-amino-3-hydroxy-N-1H-pyrrol-1-ylpropanamide.

16. The compound as defined in claim 1 which is (±)-phenylmethyl-[1-(hydroxymethyl)-2-oxo-2-(1H-pyrrol-1-ylamino)ethyl]carbamate.

17. The compound as defined in claim 1 which is (±)-2-amino-3-hydroxy-N-1H-pyrrol-1-ylpropanamide.

18. The compound as defined in claim 1 which is (±)-phenylmethyl-[1-(acetyloxymethyl)-2-oxo-2-(1H-pyrrol-1-ylamino)ethyl]carbamate.

19. The compound as defined in claim 1 which is (±)-3-(acetyloxy)-2-amino-N-1H-pyrrol-1-ylpropanamide.

20. The compound as defined in claim 1 which is 1,1-dimethylethyl-[4-oxo-4-(1H-pyrrol-1-ylamino)butyl]carbamate.

21. The compound as defined in claim 1 which is 1,1-dimethylethyl-[3-oxo-3-(1H-pyrrol-1-ylamino)propyl]carbamate.

22. The compound as defined in claim 1 which is 1,1-dimethylethyl-[2-(2-chloro-1H-pyrrol-1-ylamino)-2-oxoethyl]carbamate.

23. The compound as defined in claim 1 which is 2-amino-N-(2-chloro-1H-pyrrol-1-yl)acetamide.

24. The compound as defined in claim 1 which is 1,1-dimethylethyl-[2-(2,5-dimethyl-1H-pyrrol-1-ylamino)-2-oxoethyl]carbamate.

25. The compound as defined in claim 1 which is 2-amino-N-(2,5-dichloro-1H-pyrrol-1-yl)acetamide.

26. The compound as defined in claim 1 which is 1,1-dimethylethyl-[2-(2-phenyl-1H-pyrrol-1-ylamino)-2-oxoethyl]carbamate.

27. The compound as defined in claim 1 which is N-(2-acetyl-1H-pyrrol-1-yl)-2-aminoacetamide.

28. The compound as defined in claim 1 which is 1,1-dimethylethyl-[2-[(2-acetyl-1H-pyrrol-1-yl)amino]-2-oxoethyl]carbamate.

29. The compound as defined in claim 1 which is phenylmethyl-[2-[(2-acetyl-1H-pyrrol-1-yl)amino]-2-oxoethyl]carbamate.

30. The compound as defined in claim 1 which is 1,1-dimethylethyl-[2-[[2-(2-methyl-1-oxopropyl)-1H-pyrrol-1-yl]amino]-2-oxoethyl]carbamate.

31. The compound as defined in claim 1 which is 2-amino-N-[2-(2-methyl-1-oxopropyl)-1H-pyrrol-1-yl]acetamide.

32. The compound as defined in claim 1 which is phenylmethyl-[2-[[2-(4-methoxybenzoyl)-1H-pyrrol-1-yl]amino]-2-oxoethyl]carbamate.

33. The compound as defined in claim 1 which is 2-amino-N-[2-(4-methoxybenzoyl)-1H-pyrrol-1-yl]acetamide.

34. The compound as defined in claim 1 which is 2-amino-N-[2-(2-methoxybenzoyl)-1H-pyrrol-1-yl]acetamide.

35. The compound as defined in claim 1 which is phenylmethyl-[2-[[2-(2-methoxybenzoyl)-1H-pyrrol-1-yl]amino]-2-oxoethyl]carbamate.

36. The compound as defined in claim 3 which is phenylmethyl-[2-oxo-2-[[2-(1H-pyrrol-2-ylcarbonyl)-1H-pyrrol-1-yl]amino]ethyl]-carbamate.

37. The compound as defined in claim 3 which is 2-amino-N-[2-(1H-pyrrol-2-ylcarbonyl)-1H-pyrrol-1-yl]acetamide.

38. The compound as defined in claim 3 which is 1,1-dimethylethyl-[2-oxo-2-[[2-(2-thienylcarbonyl)-1H-pyrrol-1-yl]amino]-ethyl]carbamate.

39. The compound as defined in claim 3 which is 2-amino-N-[2-(2-thienylcarbonyl)-1H-pyrrol-1-yl]acetamide.

40. The compound as defined in claim 3 which is 1,1-dimethylethyl-[2-oxo-2-[[2-(3-methyl-2-thienylcarbonyl)-1H-pyrrol-1-yl]amino]ethyl]carbamate.

41. A method of treating a patient in need of relief from a memory disorder which comprises administering to such a patient an effective amount of a compound as defined in claim 1.

42. A method of enhancing memory and learning in a patient which comprises administering to such a patient an effective amount of a compound as defined in claim 1.

43. A method of treating a condition which is ameliorated by the use of a glycine partial agonist which comprises administering to a patient an effective amount to relieve said condition of a compound as defined in claim 1.

* * * * *